US008999326B2

(12) United States Patent
Simon

(10) Patent No.: US 8,999,326 B2
(45) Date of Patent: Apr. 7, 2015

(54) ONCOTHERAPEUTIC APPLICATION OF INHIBITORS OF HIGH-AFFINITY GLUCOSE TRANSPORTERS

(75) Inventor: George R. Simon, Huntingdon Valley, PA (US)

(73) Assignee: University of South Florida, Tampa, FL (US)

( * ) Notice: Subject to any disclaimer, the term of this patent is extended or adjusted under 35 U.S.C. 154(b) by 514 days.

(21) Appl. No.: 12/673,677

(22) PCT Filed: Aug. 15, 2008

(86) PCT No.: PCT/US2008/073361
§ 371 (c)(1),
(2), (4) Date: Mar. 25, 2010

(87) PCT Pub. No.: WO2009/026169
PCT Pub. Date: Feb. 26, 2009

(65) Prior Publication Data
US 2011/0104249 A1 May 5, 2011

Related U.S. Application Data

(60) Provisional application No. 60/956,551, filed on Aug. 17, 2007.

(51) Int. Cl.
*A61K 9/127* (2006.01)
*A61K 31/39* (2006.01)
*A61K 31/53* (2006.01)

(52) U.S. Cl.
CPC .............. *A61K 31/39* (2013.01); *A61K 31/53* (2013.01)

(58) Field of Classification Search
None
See application file for complete search history.

(56) References Cited

U.S. PATENT DOCUMENTS 7,001,735 B2 * 2/2006 Charron et al. .............. 435/7.23

OTHER PUBLICATIONS

Simon, G., S. Rastogi, and S. Chellappan. "380 Poster Glut1 antibodies decrease proliferation and enhance the induction of apoptosis in human non small cell lung cancer (NSCLC) and breast cancer (BC) cell lines." European Journal of Cancer Supplements 4.12 (2006): 117.*
Perez. Paclitaxel in breast cancer. The Oncologist. 3:373-389, 1998.*
ATCC MCF7 product sheet, retrieved online May 6, 2013 from http://www.atcc.org/products/all/HTB-22.aspx#11F1A8C17A7A4FB8A36940C154A9B585.*
Burdall et al. Breast cancer cell lines: friend or foe? Breast Cancer Research. 5:89-95, Feb. 3, 2003.*
Heppner et al. Tumor heterogeneity: biological implications and therapeutic consequences. Cancer Metastasis Review; 2:5-23, 1983.*

Goldman et al. GLUT1 and GLUT8 in endometrium and endometrial adenocarcinoma. Modern Patholgy.19:1429-1436, Aug. 4, 2006.*
Grover-McKay et al. Role for glucose transporter 1 protein in human breast cancer. Pathology Oncology Research. 4(2): 115-120. 1998.*
AFT RL, Zhang FW, Gius D. Evaluation of 2-deoxy-D-glucose as a chemotherapeutic agent: mechanism of cell death. Br J Cancer 2002;87:805-12.
Chan J Y-W, Kong S-K, Choy Y-M, Lee C-Y, Fung K-P, Inhbition of Glucose Transporter Gene Expression by Antisense Nucleic Acids in HL-60 Leukemia Cells. *Life Sciences* 1999:65:1:63-70.
Chen C-P, Li X-X, Zhang L-R, Min J-M, Chan J Y-W, Fung K-P, Wang S-Q, Zhang L, Synthesis of Antisense Oligonucleotide-Peptide Conjugate Targeting to Glut-1 in HepG-2 and MCF-7 Cells. *Bioconjugate Chem* 2002 13(3), 525-529.
Clavo AC, Brown RS, Wahl RL. Fluorodeoxyglucose uptake in human cancer cell lines is increased by hypoxia. *J Nucl Med* 1995;36:1625-32.
Dang CV, Semenza GL. Oncogenic alterations of metabolism. *Trends Biochem Sci* 1999;24:68-72.
Dasgupta P, Kinkade R. Joshi Bharat, Decook C, Haura E, Chellappan S, Nicotine inhibits apoptosis induced by chemotherapeutic drugs by up-regulating XIAP and surviving. *PNAS* 2006 103:16:6332-6337.
Detterbeck FC, Falen S. Rivera MP, Halle JS, Socinski MA. Seeking a home for a PET, part 2: Defining the appropriate place for positron emission tomography imaging in the staging of patients with suspected lung cancer. *Chest* 2004;125:2300-8.
Elstrom RL, Bauer DE, Buzzai M et al. Akt stimulates aerobic glycolysis in cancer cells. *Cancer Res* 2004;64:3892-9.
Evans A, Bates V, Troy H, et al. Glut-1 as a therapeutic target: increased chemoresistance and HIF-1-independent link with cell turnover is revealed through Compare analysis and metabolomic studies. *Cancer Chemnother Pharmacol* (2008) 61:377-393.
Gambhir SS. Molecular imaging of cancer with positron emission tomography. *Nat Rev Cancer* 2002;2:683-93.
Gazdar AF, Environmental tobacco smoke, carcinogenesis, and angiogenesis: A double whammy? *Cancer Cell* 2003 4: 159-160.
Jin Q, Agrawal L, Vanhorn-Ali Z, Alkhatib G, GLUT-1-independent infection of the glioblastoma/astroglioma U87 cells by the human T cell leukemia virus type 1. *Virology* 2006; 353: 99-110.
Matsuzu K, Segade F, Matsuzu U, Carter A, Bowden DW, Perrier NO. Differential expression of glucose transporters in normal and pathologic thyroid tissue. *Thyroid* 2004; 14:806-12.
Noguchi Y, Okamoto T, Marat D et al. Expression of facilitative glucose transporter 1 mRNA in colon cancer was not regulated by k-ras. *Cancer Lett* 2000;154: 137-42.

(Continued)

*Primary Examiner* — Brian J Gangle
*Assistant Examiner* — Andrea McCollum
(74) *Attorney, Agent, or Firm* — Saliwanchik, Lloyd & Eisenschenk

(57) ABSTRACT

The subject invention concerns materials and methods for treating oncological disorders in a person or animal using any agent or compound that inhibits uptake of glucose into a cell. The subject invention also concerns methods for inducing apoptosis and inhibiting the proliferation or survival of a cell. In one embodiment, the methods comprise administering an effective amount of an agent or compound that inhibits the activity of one or more glucose transporter proteins, such as Glut-1. An antibody that binds to and inhibits a glucose transporter protein can be used in the present methods.

26 Claims, 19 Drawing Sheets

(56) References Cited

OTHER PUBLICATIONS

Noguchi Y, Saito A, Miyagi Y et al. Suppression of facilitative glucose transporter 1 mRNA can suppress tumor growth. *Cancer Lett* 2000; 154: 175-82.

Russo VC, Kobayashi K, Najdovska S, Baker NL, Werther GA. Neuronal protection from glucose deprivation via modulation of glucose transport and inhibition of apoptosis: a role for the insulin-like growth factor system. *Brain Res* 2004;1009:40-53.

Suganuma N, Segade F, Matsuzu K, Bowden DW. Differential expression of facilitative glucose transporters in normal and tumour kidney tissues. *BJU Int* 2007;99: 1143-9.

Vukanovic J, Passaniti A, Hirata T, Traystman RJ, Hartley-ASP B, Isaacs JT, Antiangiogenic Effects of the Quinolint-3-Carboxamide Linomide[1]. *Cancer Research* 1993; 53: 1833-1837.

Warburg O. On the origin of cancer cells. *Science* 1956;123:309-14.

Yang N-C, Ho W-M, Chen Y-H, Hu M-L, A Convenient One-Step Extraction of Cellular ATP Using Boiling Water for the Luciferin—Luciferase Assay of ATP. *Analytical Biochemistry* 2002; 306: 323-327.

Younes M, Brown RW, Mody DR, Fernandez L, Laucirica R. Gluti expression in human breast carcinoma: correlation with known prognostic markers. *Anticancer Res* 1995;15:2895-8.

Younes M, Lechago LV, Lechago J. Overexpression of the human erythrocyte glucose transporter occurs as a late event in human colorectal carcinogenesis and is associated with an increased incidence of lymph node metastases. *Clin Cancer Res* 1996;2:1151-4.

Younes M, Lechago LV, Somoano JR, Mosharaf M, Lechago 1. Wide expression of the human erythrocyte glucose transporter Glutl in human cancers. *Cancer Res* 1996;56: 1164-7.

Detterbeck FC, Falen S, Rivera MP, Halle JS, Socinski MA. Seeking a home for a PET, part 1: Defining the appropriate place for positron emission tomography imaging in the diagnosis of pulmonary nodules or masses. *Chest* 2004;125:2294-2299.

Rastogi S et al., "Glut-1 antibodies induce growth arrest and apoptosis in human cancer cell lines" *Cancer Letters*, 2007, 257:244-251.

Doege H et al., "GLUT8, a Novel Member of the Sugar Transport Facilitator Family with Glucose Transport Activity" *The Journal of Biological Chemistry*, 2000, 275(21):16275-16280.

Wood IS and Trayhurn P, "Glucose transporters (GLUT and SGLT): expanded families of sugar transport proteins" *British Journal of Nutrition*, 2003, 89:3-9.

Schmidt S et al., "GLUT8, the enigmatic intracellular hexose transporter" *American Journal of Physiology—Endocrinology and Metabolism*, 2009, 296:E614-E618.

\* cited by examiner

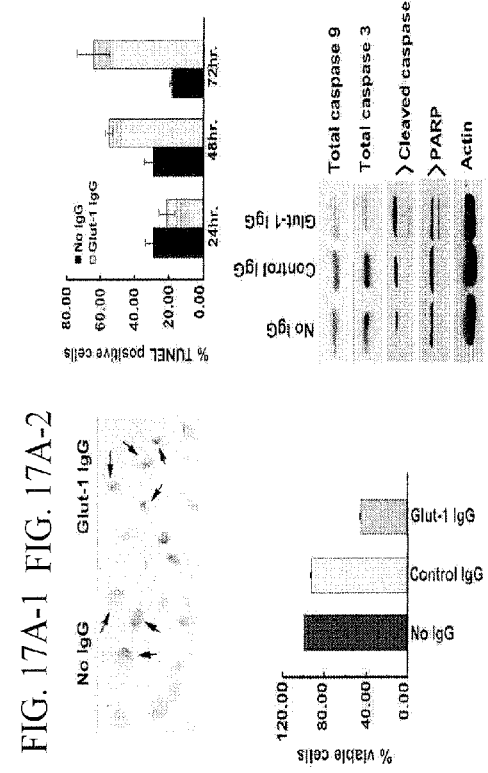

ONCOTHERAPEUTIC APPLICATION OF INHIBITORS OF HIGH-AFFINITY GLUCOSE TRANSPORTERS

CROSS-REFERENCE TO RELATED APPLICATIONS

The present application is the National Stage of International Application Number PCT/US2008/073361, filed Aug. 15, 2008, which claims the benefit of U.S. Provisional Application Ser. No. 60/956,551, filed Aug. 17, 2007, which is hereby incorporated by reference herein in its entirety, including any figures, tables, nucleic acid sequences, amino acid sequences, and drawings.

BACKGROUND OF THE INVENTION

Cancer is very difficult to cure after significant metastasis. Currently available treatments can prolong survival and improve quality of life in most metastatic cancers. This is achieved by using several treatment modalities either sequentially or in combination. Adding another novel therapeutic modality could potentially benefit millions of individuals fighting this disease.

Neoplastic cancer cells use glucose as the primary fuel to meet high energy demands. Cancer cells aggressively divert glucose from normal cells by up-regulating high affinity glucose transporters like Glucose Transporter 1 in the cell membrane.

Acquisition of the glycolytic phenotype has been shown to correlate with increased tumor aggressiveness and poor patient prognosis in several tumor types (Younes et al., 1995). Facilitative glucose uptake is achieved by trans-membrane transporters, termed Glut-1-5 and Glut-12, which are protein products of their respective GLUT genes. Although more than one Glut may be expressed by a particular cell type, tumors frequently over express Glut-1, which is a high affinity glucose transporter (Clavo et al., 1995). Human tumor cell lines, in response to hypoxia, increase glucose uptake by up-regulating membranous expression of the Glut-1 glucose transporter. This ability to survive periods of hypoxia confers tumors with an aggressive malignant phenotype enabling it to be resistant to both chemotherapy and radiotherapy and consequently poor overall survival. In several tumors including, NSCLC, colon cancer, bladder cancer, breast cancer and thyroid cancers, increased Glut-1 expression not only confers a malignant phenotype but also predicts for inferior survival (Younes et al., 1995; Younes et al. 1996a; Younes et al., 1996b).

BRIEF SUMMARY OF THE INVENTION

The subject invention concerns materials and methods for treating oncological disorders in a person or animal using agents or compounds that inhibit uptake of glucose into a cell, wherein the method comprises administering a therapeutically effective amount of the compound or agent of the invention. In one embodiment, the agent or compound is one that inhibits one or more glucose transporter (Glut) proteins. In a further embodiment, the glucose transporter protein is a high-affinity glucose transporter protein. In a specific embodiment, the glucose transporter protein is the Glut-1 protein.

The subject invention also concerns methods for inducing apoptosis of a cell comprising contacting the cell with an effective amount of an agent or compound that inhibits uptake of glucose into the cell. In one embodiment, the cell is a cell that constitutively expresses or overexpresses one or more glucose transporter proteins. In one embodiment, the cell is a cancer or tumor cell. In a specific embodiment, the agent or compound is an antibody, or an antigen binding fragment thereof, that binds to and inhibits a glucose transporter protein. In a more specific embodiment, the protein is Glut-1.

The subject invention also concerns methods for inhibiting the proliferation or survival of a cell comprising contacting the cell with an effective amount of an agent or compound that inhibits uptake of glucose into the cell. In one embodiment, the cell is a cell that constitutively expresses or overexpresses one or more glucose transporter proteins. In one embodiment, the cell is a cancer or tumor cell. In a specific embodiment, the agent or compound is an antibody, or an antigen binding fragment thereof, that binds to and inhibits a glucose transporter protein. In a more specific embodiment, the protein is Glut-1.

The subject invention also concerns methods for treating a person or animal having a disorder that is associated with constitutive expression and/or overexpression of one or more glucose transporter proteins in a cell, wherein the methods comprise administering an effective amount of an agent or compound that inhibits the activity of one or more glucose transporter proteins.

BRIEF DESCRIPTION OF THE DRAWINGS

FIGS. 17A-1, 17A-2, and 17B-17D—Treatment with anti-Glut-1 antibody induces apoptosis in comparison to treatment with control IgG1 antibody as demonstrated by tissue culture panels in FIGS. 17A-1 and 17A-2. Optimal apoptosis is seen in at 72 hours as demonstrated by FIG. 17B. Decrease in percentage of viable cells when treated with Glut-1 antibody is demonstrated by FIG. 17C. In FIG. 17D, apotosis induced by Glut-1 antibody is demonstrated by a decrease in total caspase 3 and 9 and cleavage of caspase 3 and PARP.

DETAILED DESCRIPTION OF THE INVENTION

Figure 1:
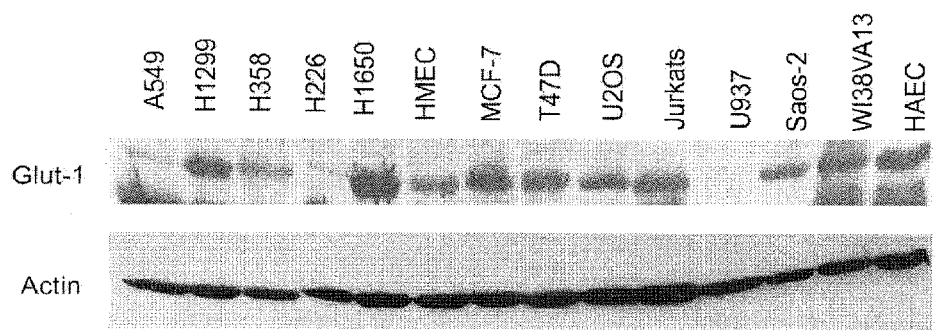
FIG. 1 shows Glut-1 expression in different cell lines. Cell lysates were prepared from various cell lines and 100 ug protein was electrophoresed and blotted nitrocellulose membrane. The lysates were boiled in 20 ul of SDS sample buffer and separated on 8% polyacrylamide gel. After semi-dry transfer to supported nitrocellulose membranes, the blots were probed with the Glut-1 monoclonal antibody. The proteins were detected by using an enhanced chemiluminescence assay system from Amersham. The blot revealed increased expression of Glut-1 in H1299, H1650, MCF-7 and T47D.

The subject invention concerns materials and methods for treating ontological and other disorders in a person or animal by administering a therapeutically effective amount of a compound, agent, or composition that inhibits uptake of glucose into a cell. The agent, compound, or composition can be any agent, compound, or composition that inhibits one or more glucose transporter (Glut) proteins, or that inhibits expression, transcription, or translation of a gene or polynucleotide encoding a Glut protein, or a polynucleotide or polypeptide that upregulates or promotes expression of a Glut gene or protein. In an exemplified embodiment, the agent is an antibody, or antigen binding fragment thereof, that binds to a Glut protein. Also contemplated within the scope of the invention are antisense oligonucleotides, siRNA, aptamers, DNAzymes (Breaker and Joyce, 1994, 1995; Carmi et al., 1996; Santoro et al., 1997; published U.S. application US 2004/0002106) and ribozymes that inhibit expression, transcription, or translation of a Glut-encoding gene or the gene product thereof, or of a polynucleotide or polypeptide that upregulates or promotes expression of a Glut gene or protein. In a further embodiment, the glucose transporter protein is a high-affinity glucose transporter protein. In a specific embodiment, the glucose transporter protein is the Glut-1 protein.

In certain embodiments of the present methods, the inhibitor compound, agent, or composition can be administered to the person or animal prior to, subsequent to, or in conjunction with chemotherapy, immunotherapy and/or radiotherapy for treatment of an oncological disorder. Methods of the invention can optionally include identifying a patient who is or may be in need of treatment of an oncological disorder. Patients in need of treatment using the methods of the present invention can be identified using standard techniques and/or assays known to those in the medical or veterinary professions, as appropriate.

In one embodiment, the Glut inhibitor used in the methods and compositions of the invention is a polynucleotide that reduces expression of one or more of Glut genes. Thus, the method involves administering an effective amount of polynucleotides that specifically target nucleotide sequence(s) within a target Glut gene(s) or the transcription product thereof. In one embodiment, the method of the invention involves reducing expression of one or more Glut genes by administering a polynucleotide specific for a Glut gene, or a gene that promotes or is associated with upregulation of expression of a Glut gene or protein, wherein the polynucleotide interferes with expression of the gene in a sequence-specific manner, to yield reduced levels of the gene product (the translated polypeptide). Preferably, the polynucleotide is a silencing double stranded ribonucleic acid (RNA) sequence, also called a small interfering RNA (siRNA) that causes degradation of the targeted RNA (RNA interference or RNAi). RNAi is an efficient process whereby double-stranded RNA (dsRNA, also referred to herein as siRNAs or ds siRNAs, for double-stranded small interfering RNAs) induces the sequence-specific degradation of targeted mRNA in animal and plant cells (Hutvagner and Zamore, 2002; Sharp, 2001). In mammalian cells, RNAi can be triggered by 21-nucleotide (nt) duplexes of small interfering RNA (siRNA) (Chiu et al., 2002; Elbashir et al., 2001), or by micro-RNAs (miRNA), functional small-hairpin RNA (shRNA), or other dsRNAs which can be expressed in vivo using DNA templates with RNA polymerase III promoters (Zeng et al., 2002; Paddison et al., 2002; Lee et al., 2002; Paul et al., 2002; Tuschl, 2002; Yu et al., 2002; McManus et al., 2002; Sui et al., 2002). Thus, in one embodiment, the polynucleotide is a double-stranded ribonucleic acid (dsRNA) that reduces expression of the Glut gene or a gene that promotes or is associated with upregulation of expression of a Glut gene or protein. In a specific embodiment, the targeted nucleotide sequence is at least a portion of a Glut gene, wherein a first strand of the dsRNA is substantially identical (e.g., at least 80% or more (i.e., 85%, 90%, 95%, etc.) sequence identity) to about 19 to 49 consecutive nucleotides of the Glut gene, and a second strand of the dsRNA is substantially complementary to the first. In another embodiment, the polynucleotide is a dsRNA comprising a first strand of nucleotides that is substantially identical to about 19 to 25 consecutive nucleotides of the Glut gene, and a second strand that is substantially complementary to the first strand. In another embodiment, a polynucleotide of the invention is a dsRNA comprising a first strand of nucleotides of at least 16 nucleotides sufficiently complementary to a target region of the Glut mRNA sequence to direct target-specific RNA interference (RNAi), and a second strand of nucleotides of at least 16 nucleotides substantially complementary to the first strand. In a further embodiment, the first strand is fully complementary to the target region of the mRNA sequence. In another embodiment, the dsRNA further comprises a loop formation comprising from about 4 to about 11 or more nucleotides that connects the first and second strands. In a specific embodiment, the first and second strands each comprise 16, 17, 18, 19, 20, 21, 22, 23, 24, 25, 26, 27, 28, 29, or 30 nucleotides. In another specific embodiment, the first and second strands each consist of 16, 17, 18, 19, 20, 21, 22, 23, 24, 25, 26, 27, 28, 29, or 30 nucleotides.

In other embodiments, the polynucleotide of the invention is an antisense nucleic acid sequence (e.g., a single stranded oligonucleotide) that is complementary to a target region sequence within or operably linked to the subject's Glut mRNA, which binds to the target region sequence and inhibits translation. The antisense oligonucleotide may be DNA or RNA, or comprise synthetic analogs of ribo-deoxynucleotides. The antisense nucleic acid sequence can be complementary to an entire coding strand of a target sequence, or to only a portion thereof. In another embodiment, the antisense nucleic acid molecule is antisense to a "noncoding region" of the coding strand of a nucleotide sequence within the target gene. Thus, the antisense oligonucleotide inhibits expression of the Glut gene. In one embodiment, the oligonucleotide has a length of about 8, 9, 10, 11, 12, 13, 14, 15, 16, 17, 18, 19, 20, 21, 22, 23, 24, 25, 26, 27, 28, 29, 30, 35, 40, 45, 50, 55, 60, 65, 70, 75, 80, 85, 90, 95, or 100 or more nucleotides. Antisense molecules can be modified (e.g., linked to an antibody or peptide) to bind to a receptor or antigen expressed by a cell.

SiRNA, antisense nucleic acid, and other nucleic acid molecules can be delivered into cells in vitro or in vivo using methods known in the art, including for example, via nanoparticles, cationic liposome transfection and electroporation. Nucleic acid molecules of the invention can also be provided in recombinant DNA expression constructs. Expression constructs can include regulatory elements that promote the expression of the nucleic acid in a host cell. Regulatory elements include, for example, promoter and enhancer sequences. Nucleic acids of the invention can also be delivered via viral vectors, such as adenovirus and adeno-associated virus.

In other embodiments, the polynucleotide of the invention is an RNA molecule having enzymatic activity (a ribozyme) that inhibits expression of the target Glut gene(s). In one embodiment, the ribozyme comprises a 5'-end flanking region having 4 to 50 nucleotides and being complementary to a 3'-end target region within the Glut mRNA; a stem-loop region, comprising a stem portion having 2 to 12 nucleotide pairs and a loop portion comprising at least 2 unpaired nucleotides; and a 3'-end flanking region having 4 to 50 nucleotides and being complementary to a 5' end target site on the substrate RNA.

The nucleic acid target of the polynucleotides (e.g., siRNA, antisense oligonucleotides, and ribozymes) of the invention may be any location within or operably linked to a Glut gene or transcript, or to a gene or transcript associated with upregulation of Glut gene or protein expression.

In one embodiment, the patient can be a human or other mammal, such as a primate (monkey, chimpanzee, ape, etc.), dog, cat, cow, pig, or horse, or other animals having an ontological disorder. Means for administering and formulating compounds of the invention for administration to a patient are known in the art, examples of which are described herein. Oncological disorders within the scope of the invention include, but are not limited to, cancer and/or tumors of the anus, bile duct, bladder, bone, bone marrow, bowel (including colon and rectum), breast, eye, gall bladder, kidney, mouth, larynx, esophagus, stomach, testis, cervix, head, neck, ovary, lung, mesothelioma, neuroendocrine, penis, skin, spinal cord, thyroid, vagina, vulva, uterus, liver, muscle, pancreas, prostate, blood cells (including lymphocytes and other immune system cells), and brain. Specific cancers contemplated for treatment with the present invention include carcinomas, Karposi's sarcoma, melanoma, mesothelioma, soft tissue sarcoma, pancreatic cancer, lung cancer, leukemia (acute lymphoblastic, acute myeloid, chronic lymphocytic, chronic myeloid, and other), and lymphoma (Hodgkin's and non-Hodgkin's), and multiple myeloma.

Examples of cancers that can be treated according to the present invention are listed in Table 1.

TABLE 1

Examples of Cancer Types

| | |
|---|---|
| Acute Lymphoblastic Leukemia, Adult | Hairy Cell Leukemia |
| Acute Lymphoblastic Leukemia, Childhood | Head and Neck Cancer |
| | Hepatocellular (Liver) Cancer, Adult |
| Acute Myeloid Leukemia, Adult | (Primary) |
| Acute Myeloid Leukemia, Childhood | Hepatocellular (Liver) Cancer, Childhood |
| Adrenocortical Carcinoma | (Primary) |
| Adrenocortical Carcinoma, Childhood | Hodgkin's Lymphoma, Adult |
| AIDS-Related Cancers | Hodgkin's Lymphoma, Childhood |
| AIDS-Related Lymphoma | Hodgkin's Lymphoma During Pregnancy |
| Anal Cancer | Hypopharyngeal Cancer |
| Astrocytoma, Childhood Cerebellar | Hypothalamic and Visual Pathway Glioma, |
| Astrocytoma, Childhood Cerebral | Childhood |
| Basal Cell Carcinoma | Intraocular Melanoma |
| Bile Duct Cancer, Extrahepatic | Islet Cell Carcinoma (Endocrine Pancreas) |
| Bladder Cancer | Kaposi's Sarcoma |
| Bladder Cancer, Childhood | Kidney (Renal Cell) Cancer |

TABLE 1-continued

Examples of Cancer Types

Bone Cancer, Osteosarcoma/Malignant Fibrous Histiocytoma
Brain Stem Glioma, Childhood
Brain Tumor, Adult
Brain Tumor, Brain Stem Glioma, Childhood
Brain Tumor, Cerebellar Astrocytoma, Childhood
Brain Tumor, Cerebral Astrocytoma/Malignant Glioma, Childhood
Brain Tumor, Ependymoma, Childhood
Brain Tumor, Medulloblastoma, Childhood
Brain Tumor, Supratentorial Primitive Neuroectodermal Tumors, Childhood
Brain Tumor, Visual Pathway and Hypothalamic Glioma, Childhood
Brain Tumor, Childhood
Breast Cancer
Breast Cancer, Childhood
Breast Cancer, Male
Bronchial Adenomas/Carcinoids, Childhood
Burkitt's Lymphoma
Carcinoid Tumor, Childhood
Carcinoid Tumor, Gastrointestinal
Carcinoma of Unknown Primary
Central Nervous System Lymphoma, Primary
Cerebellar Astrocytoma, Childhood
Cerebral Astrocytoma/Malignant Glioma, Childhood
Cervical Cancer
Childhood Cancers
Chronic Lymphocytic Leukemia
Chronic Myelogenous Leukemia
Chronic Myeloproliferative Disorders
Colon Cancer
Colorectal Cancer, Childhood
Cutaneous T-Cell Lymphoma, see Mycosis Fungoides and Sézary Syndrome
Endometrial Cancer
Ependymoma, Childhood
Esophageal Cancer
Esophageal Cancer, Childhood
Ewing's Family of Tumors
Extracranial Germ Cell Tumor, Childhood
Extragonadal Germ Cell Tumor
Extrahepatic Bile Duct Cancer
Eye Cancer, Intraocular Melanoma
Eye Cancer, Retinoblastoma
Gallbladder Cancer
Gastric (Stomach) Cancer
Gastric (Stomach) Cancer, Childhood
Gastrointestinal Carcinoid Tumor
Germ Cell Tumor, Extracranial, Childhood
Germ Cell Tumor, Extragonadal
Germ Cell Tumor, Ovarian
Gestational Trophoblastic Tumor
Glioma, Adult
Glioma, Childhood Brain Stem
Glioma, Childhood Cerebral Astrocytoma
Glioma, Childhood Visual Pathway and Hypothalamic
Skin Cancer (Melanoma)
Skin Carcinoma, Merkel Cell
Small Cell Lung Cancer
Small Intestine Cancer
Soft Tissue Sarcoma, Adult
Soft Tissue Sarcoma, Childhood
Squamous Cell Carcinoma, see Skin Cancer (non-Melanoma)
Squamous Neck Cancer with Occult
Kidney Cancer, Childhood
Laryngeal Cancer
Laryngeal Cancer, Childhood
Leukemia, Acute Lymphoblastic, Adult
Leukemia, Acute Lymphoblastic, Childhood
Leukemia, Acute Myeloid, Adult
Leukemia, Acute Myeloid, Childhood
Leukemia, Chronic Lymphocytic
Leukemia, Chronic Myelogenous
Leukemia, Hairy Cell
Lip and Oral Cavity Cancer
Liver Cancer, Adult (Primary)
Liver Cancer, Childhood (Primary)
Lung Cancer, Non-Small Cell
Lung Cancer, Small Cell
Lymphoma, AIDS-Related
Lymphoma, Burkitt's
Lymphoma, Cutaneous T-Cell, see Mycosis Fungoides and Sézary Syndrome
Lymphoma, Hodgkin's, Adult
Lymphoma, Hodgkin's, Childhood
Lymphoma, Hodgkin's During Pregnancy
Lymphoma, Non-Hodgkin's, Adult
Lymphoma, Non-Hodgkin's, Childhood
Lymphoma, Non-Hodgkin's During Pregnancy
Lymphoma, Primary Central Nervous System
Macroglobulinemia, Waldenström's
Malignant Fibrous Histiocytoma of Bone/Osteosarcoma
Medulloblastoma, Childhood
Melanoma
Melanoma, Intraocular (Eye)
Merkel Cell Carcinoma
Mesothelioma, Adult Malignant
Mesothelioma, Childhood
Metastatic Squamous Neck Cancer with Occult Primary
Multiple Endocrine Neoplasia Syndrome, Childhood
Multiple Myeloma/Plasma Cell Neoplasm
Mycosis Fungoides
Myelodysplastic Syndromes
Myelodysplastic/Myeloproliferative Diseases
Myelogenous Leukemia, Chronic
Myeloid Leukemia, Adult Acute
Myeloid Leukemia, Childhood Acute
Myeloma, Multiple
Myeloproliferative Disorders, Chronic
Nasal Cavity and Paranasal Sinus Cancer
Nasopharyngeal Cancer
Nasopharyngeal Cancer, Childhood
Neuroblastoma
Non-Hodgkin's Lymphoma, Adult
Non-Hodgkin's Lymphoma, Childhood
Non-Hodgkin's Lymphoma During Pregnancy
Non-Small Cell Lung Cancer
Oral Cancer, Childhood
Oral Cavity Cancer, Lip and
Oropharyngeal Cancer
Osteosarcoma/Malignant Fibrous Histiocytoma of Bone
Ovarian Cancer, Childhood
Ovarian Epithelial Cancer
Ovarian Germ Cell Tumor
Ovarian Low Malignant Potential Tumor
Pancreatic Cancer
Pancreatic Cancer, Childhood
Pancreatic Cancer, Islet Cell
Paranasal Sinus and Nasal Cavity Cancer
Parathyroid Cancer
Penile Cancer
Pheochromocytoma
Pineoblastoma and Supratentorial Primitive Neuroectodermal Tumors, Childhood
Pituitary Tumor
Plasma Cell Neoplasm/Multiple Myeloma
Pleuropulmonary Blastoma

TABLE 1-continued

Examples of Cancer Types

| | |
|---|---|
| Primary, Metastatic | Pregnancy and Breast Cancer |
| Stomach (Gastric) Cancer | Pregnancy and Hodgkin's Lymphoma |
| Stomach (Gastric) Cancer, Childhood | Pregnancy and Non-Hodgkin's Lymphoma |
| Supratentorial Primitive Neuroectodermal Tumors, Childhood | Primary Central Nervous System Lymphoma |
| | Prostate Cancer |
| T-Cell Lymphoma, Cutaneous, see Mycosis Fungoides and Sézary Syndrome | Rectal Cancer |
| | Renal Cell (Kidney) Cancer |
| | Renal Cell (Kidney) Cancer, Childhood |
| Testicular Cancer | Renal Pelvis and Ureter, Transitional Cell Cancer |
| Thymoma, Childhood | |
| Thymoma and Thymic Carcinoma | Retinoblastoma |
| Thyroid Cancer | Rhabdomyosarcoma, Childhood |
| Thyroid Cancer, Childhood | Salivary Gland Cancer |
| Transitional Cell Cancer of the Renal Pelvis and Ureter | Salivary Gland Cancer, Childhood |
| | Sarcoma, Ewing's Family of Tumors |
| Trophoblastic Tumor, Gestational | Sarcoma, Kaposi's |
| Unknown Primary Site, Carcinoma of, Adult | Sarcoma, Soft Tissue, Adult |
| | Sarcoma, Soft Tissue, Childhood |
| Unknown Primary Site, Cancer of, Childhood | Sarcoma, Uterine |
| | Sezary Syndrome |
| Unusual Cancers of Childhood | Skin Cancer (non-Melanoma) |
| Ureter and Renal Pelvis, Transitional Cell Cancer | Skin Cancer, Childhood |
| Urethral Cancer | |
| Uterine Cancer, Endometrial | |
| Uterine Sarcoma | |
| Vaginal Cancer | |
| Visual Pathway and Hypothalamic Glioma, Childhood | |
| Vulvar Cancer | |
| Waldenström's Macroglobulinemia | |
| Wilms' Tumor | |

The subject invention also concerns methods for treating a person or animal having a disorder that is associated with constitutive expression and/or overexpression of one or more glucose transporter proteins in a cell, wherein the methods comprise administering an effective amount of an agent, compound, or composition that inhibits the activity of one or more glucose transporter proteins. The agent or compound can be any agent or compound that inhibits one or more glucose transporter (Glut) proteins, or that inhibits expression of a gene or polynucleotide encoding a Glut protein.

The subject invention also concerns methods for inducing apoptosis of a cell comprising contacting the cell with an effective amount of an agent, compound, or composition that inhibits uptake of glucose into the cell. In one embodiment, the cell is a cell that constitutively expresses or overexpresses one or more glucose transporter proteins. In one embodiment, the cell is a cancer or tumor cell. The agent or compound can be any agent or compound that inhibits one or more glucose transporter (Glut) proteins, or that inhibits expression of a gene or polynucleotide encoding a Glut protein. In a specific embodiment, the agent or compound is an antibody, or an antigen binding fragment thereof, that binds to and inhibits a glucose transporter protein. In a more specific embodiment, the protein is Glut-1. In one embodiment, the cell is a human cell or other mammalian cell. Cancer cells that can be inhibited or killed using the subject methods include those cells that are metastatic in nature. Thus, inhibition of metastasis of a cancer or tumor cell is also contemplated by the present invention. The methods can be practiced in vitro or in vivo.

The subject invention also concerns methods for inhibiting the proliferation or survival of a cell comprising contacting the cell with an effective amount of an agent, compound, or composition that inhibits uptake of glucose into the cell. In one embodiment, the cell is a cell that constitutively expresses or overexpresses one or more glucose transporter proteins. In one embodiment, the cell is a cancer or tumor cell. The agent or compound can be any agent or compound that inhibits one or more glucose transporter (Glut) proteins, or that inhibits expression of a gene or polynucleotide encoding a Glut protein. In a specific embodiment, the agent or compound is an antibody, or an antigen binding fragment thereof, that binds to and inhibits a glucose transporter protein. In a more specific embodiment, the protein is Glut-1. In one embodiment, the cell is a human cell or other mammalian cell. Cancer cells that can be inhibited or killed using the subject methods include those cells that are metastatic in nature. Thus, inhibition of metastasis of a cancer or tumor cell is also contemplated by the present invention. The methods can be practiced in vitro or in vivo.

The term "antibody" includes antibody fragments (an antigen binding portion of an antibody), as are known in the art, including Fab or $Fab_2$, single chain antibodies (Fv for example), chimeric antibodies, etc., either produced by the modification of whole antibodies or those synthesized de novo using recombinant DNA technologies. The term "antigen-binding fragment" or "antigen-binding portion" of an antibody (or simply "antibody portion," or "fragment"), as used herein, refers to one or more fragments of a full-length antibody that retain the ability to specifically bind to an antigen. Examples of binding fragments encompassed within the term "antigen-binding fragment" of an antibody include (i) a Fab fragment, a monovalent fragment consisting of the VL, VII, CL and CH1 domains; (ii) a F(ab')2 fragment, a bivalent fragment comprising two Fab fragments linked by a disulfide bridge at the hinge region; (iii) a Fd fragment consisting of the VH and CH1 domains; (iv) a Fv fragment consisting of the VL and VII domains of a single arm of an antibody, (v) a dAb fragment (Ward et al., 1989), which consists of a VH domain; and (vi) an isolated complementarity determining region (CDR). Furthermore, although the two domains of the Fv fragment, VL and VH, are coded for by separate nucleic acids, they can be joined, using recombinant methods, by a synthetic linker that enables them to be made as a single protein chain in which the VL and VII regions pair to form monovalent molecules (known as single chain Fv (scFv); see e.g., Bird et al., 1988; Huston et al., 1988). Such single chain antibodies are also intended to be encompassed within the term "antigen-binding fragment" or "antigen-binding portion" or "fragment" of an antibody. These antibody fragments are obtained using conventional techniques known to those with skill in the art, and the fragments are screened for utility in the same manner as are intact antibodies. The term "monoclonal antibody" or "monoclonal antibody composition", as used herein, refers to a population of antibody molecules that contain only one species of an antigen binding site capable of immunoreacting with a particular epitope. A monoclonal antibody composition thus typically displays a single binding affinity for a particular protein with which it immunoreacts.

Anti-protein/anti-peptide antisera or monoclonal antibodies can be made as described herein by using standard protocols (See, for example, Harlow and Lane, 1988). For example, a Glut protein, or a portion or fragment thereof, can be used as an immunogen to generate antibodies that bind the component using standard techniques for polyclonal and monoclonal antibody preparation. The full-length component protein can be used or, alternatively, antigenic peptide fragments of the component can be used as immunogens.

Typically, a peptide is used to prepare antibodies by immunizing a suitable subject, (e.g., rabbit, goat, mouse or other mammal) with the immunogen. An appropriate immunogenic preparation can contain, for example, a recombinant Glut protein or peptide or a chemically synthesized protein or peptide. The preparation can further include an adjuvant, such as Freund's complete or incomplete adjuvant, or one or more similar immunostimulatory agents. Immunization of a suitable subject with an immunogenic component or fragment preparation induces a polyclonal antibody response.

Additionally, antibodies produced by genetic engineering methods, such as chimeric and humanized monoclonal antibodies, comprising both human and non-human portions, which can be made using standard recombinant DNA techniques, can be used. Such chimeric and humanized monoclonal antibodies can be produced by genetic engineering using standard DNA techniques known in the art, for example using methods described in U.S. Pat. No. 4,816,567; Better et al., 1988; Liu et al., 1987b; Liu et al., 1987a; Sun et al., 1987; Nishimura et al., 1987; Wood et al., 1985; Shaw et al., 1988; Morrison, 1985; Oi et al., 1986; U.S. Pat. No. 5,225,539; Jones et al., 1986; Verhoeyan et al., 1988; and Beidler et al., 1988.

In addition, a human monoclonal antibody directed against Glut proteins can be made using standard techniques. For example, human monoclonal antibodies can be generated in transgenic mice or in immune deficient mice engrafted with antibody-producing human cells. Methods of generating such mice are described, for example, in Wood et al. PCT publication WO 91/00906, Kucherlapati et al. PCT publication WO 91/10741; Lonberg et al. PCT publication WO 92/03918; Kay et al. PCT publication WO 92/03917; Kay et at. PCT publication WO 93/12227; Kay et al. PCT publication 94/25585; Rajewsky et al. PCT publication WO 94/04667; Ditullio et al. PCT publication WO 95/17085; Lonberg et al., 1994; Green et al., 1994; Morrison et al., 1994; Bruggeman et al., 1993; Choi et al., 1993; Tuaillon et al., 1993; Bruggeman et al., 1991; Duchosal et al. PCT publication WO 93/05796; U.S. Pat. No. 5,411,749; McCune et al., 1988, Kamel-Reid et al., 1988; Spanopoulou, 1994; and Shinkai et al., 1992. A human antibody-transgenic mouse or an immune deficient mouse engrafted with human antibody-producing cells or tissue can be immunized with Glut proteins or an antigenic peptide thereof, and splenocytes from these immunized mice can then be used to create hybridomas. Methods of hybridoma production are well known.

Human monoclonal antibodies can also be prepared by constructing a combinatorial immunoglobulin library, such as a Fab phage display library or a say phage display library, using immunoglobulin light chain and heavy chain cDNAs prepared from mRNA derived from lymphocytes of a subject (see, e.g., McCafferty et al. PCT publication WO 92/01047; Marks et al., 1991; and Griffiths et al., 1993). In addition, a combinatorial library of antibody variable regions can be generated by mutating a known human antibody. For example, a variable region of a human antibody known to bind a Glut protein can be mutated by, for example, using randomly altered mutagenized oligonucleotides, to generate a library of mutated variable regions which can then be screened to bind to Glut proteins. Methods of inducing random mutagenesis within the CDR regions of immunoglobin heavy and/or light chains, methods of crossing randomized heavy and light chains to form pairings and screening methods can be found in, for example, Barbas et al. PCT publication WO 96/07754; Barbas et al., 1992.

Aptamers are molecules that bind to a specific target molecule. Aptamers can be composed of nucleic acid (e.g., DNA or RNA) or they can be peptides or polypeptides. Methods for preparing aptamers to a target molecule are known in the art and have been described, for example, in U.S. Pat. Nos. 5,475,096; 5,270,163; 5,707,796; 5,763,177; 6,011,577; 5,580,737; 5,567,588; and 5,840,867. Aptamers contemplated within the scope of the present invention include those that bind to a Glut protein or a gene or polynucleotide encoding a Glut protein, or to a polynucleotide or polypeptide that upregulates or promotes expression of a Glut gene or protein.

While inhibitor compounds or agents of the invention can be administered as isolated compounds or agents, these compounds can also be administered as part of a pharmaceutical composition. The subject invention thus further provides compositions comprising one or more compounds or agents in association with at least one pharmaceutically acceptable carrier. The pharmaceutical composition can be adapted for various routes of administration, such as enteral, parenteral, intravenous, intramuscular, topical, subcutaneous, and so forth. Administration can be continuous or at distinct intervals, as can be determined by a person of ordinary skill in the art.

The inhibitor compounds or agents of the invention can be formulated according to known methods for preparing pharmaceutically useful compositions. Formulations are described in a number of sources which are well known and readily available to those skilled in the art. For example, *Remington's Pharmaceutical Science* (Martin 1995) describes formulations which can be used in connection with the subject invention. Formulations suitable for administration include, for example, aqueous sterile injection solutions, which may contain antioxidants, buffers, bacteriostats, and solutes that render the formulation isotonic with the blood of the intended recipient; and aqueous and nonaqueous sterile suspensions which may include suspending agents and thickening agents. The formulations may be presented in unit-dose or multi-dose containers, for example sealed ampoules and vials, and may be stored in a freeze dried (lyophilized) condition requiring only the condition of the sterile liquid carrier, for example, water for injections, prior to use. Extemporaneous injection solutions and suspensions may be prepared from sterile powder, granules, tablets, etc. It should be understood that in addition to the ingredients particularly mentioned above, the compositions of the subject invention can include other agents conventional in the art having regard to the type of formulation in question.

The compounds and agents of the present invention include all hydrates and salts that can be prepared by those of skill in the art. Under conditions where the compounds and agents of the present invention are sufficiently basic or acidic to form stable nontoxic acid or base salts, administration of the compounds as salts may be appropriate. Examples of pharmaceutically acceptable salts are organic acid addition salts formed with acids that form a physiological acceptable anion, for example, tosylate, methanesulfonate, acetate, citrate, malonate, tartarate, succinate, benzoate, ascorbate, alpha-ketoglutarate, and alpha-glycerophosphate. Suitable inorganic salts may also be formed, including hydrochloride, sulfate, nitrate, bicarbonate, and carbonate salts.

Pharmaceutically acceptable salts of a compound or agent may be obtained using standard procedures well known in the art, for example, by reacting a sufficiently basic compound such as an amine with a suitable acid affording a physiologically acceptable anion. Alkali metal (for example, sodium, potassium or lithium) or alkaline earth metal (for example calcium) salts of carboxylic acids can also be made.

Therapeutic application of compounds and/or agents and compositions containing them can be accomplished by any suitable therapeutic method and technique presently or prospectively known to those skilled in the art. Further, compounds and agents of the invention have use as starting materials or intermediates for the preparation of other useful compounds and compositions.

Compounds and agents of the invention, and compositions thereof, may be locally administered at one or more anatomical sites, such as sites of unwanted cell growth (such as a tumor site or benign skin growth, e.g., injected or topically applied to the tumor or skin growth) or sites of fungal infection, optionally in combination with a pharmaceutically acceptable earlier such as an inert diluent. Compounds and agents of the invention, and compositions thereof, may be systemically administered, such as intravenously or orally, optionally in combination with a pharmaceutically acceptable carrier such as an inert diluent, or an assimilable edible carrier for oral delivery. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, aerosol sprays, and the like.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as) sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

Compounds and agents and compositions of the invention, including pharmaceutically acceptable salts or analogs thereof, can be administered intravenously, intramuscularly, or intraperitoneally by infusion or injection. Solutions of the active agent or its salts can be prepared in water, optionally mixed with a nontoxic surfactant. Dispersions can also be prepared in glycerol, liquid polyethylene glycols, triacetin, and mixtures thereof and in oils. Under ordinary conditions of storage and use, these preparations can contain a preservative to prevent the growth of microorganisms.

The pharmaceutical dosage forms suitable for injection or infusion can include sterile aqueous solutions or dispersions or sterile powders comprising the active ingredient which are adapted for the extemporaneous preparation of sterile injectable or infusible solutions or dispersions, optionally encapsulated in liposomes. The ultimate dosage form should be sterile, fluid and stable under the conditions of manufacture and storage. The liquid carrier or vehicle can be a solvent or liquid dispersion medium comprising, for example, water, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. Optionally, the prevention of the action of microorganisms can be brought about by various other antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the inclusion of agents that delay absorption, for example, aluminum monostearate and gelatin.

Sterile injectable solutions are prepared by incorporating a compound and/or agent of the invention in the required amount in the appropriate solvent with various other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, compounds and agents of the invention may be applied in as a liquid or solid. However, it will generally be desirable to administer them topically to the skin as compositions, in combination with a dermatologically acceptable carrier, which may be a solid or a liquid. Compounds and agents and compositions of the subject invention can be applied topically to a subject's skin to reduce the size (and may include complete removal) of malignant or benign growths, or to treat an infection site. Compounds and agents of the invention can be applied directly to the growth or infection site. Preferably, the compounds and agents are applied to the growth or infection site in a formulation such as an ointment, cream, lotion, solution, tincture, or the like. Drug delivery systems for delivery of pharmacological substances to dermal lesions can also be used, such as that described in U.S. Pat. No. 5,167,649.

Useful solid carriers include finely divided solids such as talc, clay, microcrystalline cellulose, silica, alumina and the like. Useful liquid carriers include water, alcohols or glycols or water-alcohol/glycol blends, in which the compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers, for example.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user. Examples of useful dermatological compositions which can be used to deliver a compound to the skin are disclosed in U.S. Pat. No. 4,608,392; U.S. Pat. No. 4,992,478; U.S. Pat. No. 4,559,157; and U.S. Pat. No. 4,820,508.

Useful dosages of the compounds and agents and pharmaceutical compositions of the present invention can be determined by comparing their in vitro activity, and in vivo activity in animal models. Methods for the extrapolation of effective dosages in mice, and other animals, to humans are known to the art; for example, see U.S. Pat. No. 4,938,949.

The present invention also concerns pharmaceutical compositions comprising a compound and/or agent of the invention in combination with a pharmaceutically acceptable earner. Pharmaceutical compositions adapted for oral, topical or parenteral administration, comprising an amount of a compound constitute a preferred embodiment of the invention. The dose administered to a patient, particularly a human, in the context of the present invention should be sufficient to achieve a therapeutic response in the patient over a reasonable time frame, without lethal toxicity, and preferably causing no more than an acceptable level of side effects or morbidity. One skilled in the art will recognize that dosage will depend upon a variety of factors including the condition (health) of the subject, the body weight of the subject, kind of concurrent treatment, if any, frequency of treatment, therapeutic ratio, as well as the severity and stage of the pathological condition.

For the treatment of oncological disorders, compounds and agents and compositions contemplated by the present invention can be administered to a patient in need of treatment prior to, subsequent to, or in combination with other antitumor or anticancer agents or substances (e.g., chemotherapeutic agents, immunotherapeutic agents, radiotherapeutic agents, cytotoxic agents, etc.) and/or with radiation therapy and/or with surgical treatment to remove a tumor. For example, compounds and agents and compositions of the present invention can be used in methods of treating cancer wherein the patient is to be treated or is or has been treated with mitotic inhibitors such as paclitaxel (TAXOL) or vinblastine, alkylating agents such as cyclophosamide or ifosfamide, antimetabolites such as 5-fluorouracil or hydroxyurea, DNA intercalators such as adriamycin or bleomycin, topoisomerase inhibitors such as etoposide or camptothecin, antiangiogenic agents such as angiostatin, antiestrogens such as tamoxifen, and/or other anti-cancer drugs or antibodies, such as, for example, imatinib (GLEEVEC) (Novartis Pharmaceuticals Corporation) and trastuzumab (HERCEPTIN) (Genentech, Inc.), respectively. These other substances or radiation treatments may be given at the same as or at different times from the compounds of this invention. Examples of other chemotherapeutic agents contemplated within the scope of the invention include, but are not limited to, altretamine, bleomycin, bortezomib (VELCADE), busulphan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib (IRESSA), gemcitabine, hydroxyurea, idarubicin, ifosfamide, imatinib (GLEEVEC), irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafur-uracil, temozolomide, thiotepa, tioguanine/thioguanine, topotecan, treosulfan, vinblastine, vincristine, vindesine, vinorelbine. In an exemplified embodiment, the chemotherapeutic agent is melphalan. Examples of immunotherapeutic agents contemplated within the scope of the invention include, but are not limited to, alemtuzumab, cetuximab (ERBITUX), gemtuzumab, iodine 131 tositumomab, rituximab, trastuzumab (HERCEPTIN). Cytotoxic agents include, for example, radioactive isotopes (e.g., $I^{131}$, $I^{125}$, $Y^{90}$, $P^{32}$, etc.), and toxins of bacterial, fungal, plant, or animal origin (e.g., ricin, botulinum toxin, anthrax toxin, aflatoxin, jellyfish venoms (e.g., box jellyfish), etc.) The subject invention also concerns methods for treating an oncological disorder comprising administering an effective amount of a compound and/or agent of the invention prior to, subsequent to, and/or in combination with administration of a chemotherapeutic agent, an immunotherapeutic agent, a radiotherapeutic agent, or radiotherapy.

Examples of some chemotherapeutic agents that can be used according to the present invention are listed in Table 2.

TABLE 2

Examples of Chemotherapeutic Agents

| | |
|---|---|
| 13-cis-Retinoic Acid | MYLOCEL (hydroxyurea) |
| 2-Amino-6- | Letrozole |
| Mercaptopurine | Neosar |
| 2-CdA | Neulasta |
| 2-Chlorodeoxyadenosine | Neumega |
| 5-fluorouracil | Neupogen |
| 5-FU | Nilandron |
| 6-TG | Nilutamide |
| 6-Thioguanine | Nitrogen Mustard |
| 6-Mercaptopurine | Novaldex |
| 6-MP | Novantrone |
| Accutane | Octreotide |
| Actinomycin-D | Octreotide acetate |
| Adriamycin | Oncospar |
| Adrucil | Oncovin |
| Agrylin | Ontak |
| Ala-Cort | Onxal |
| Aldesleukin | Oprevelkin |
| Alemtuzumab | Orapred |
| Alitretinoin | Orasone |
| Alkaban-AQ | Oxaliplatin |
| Alkeran | Paclitaxel |
| All-transretinoic acid | Pamidronate |
| Alpha interferon | Panretin |
| Altretamine | Paraplatin |
| Amethopterin | Pediapred |
| Amifostine | PEG Interferon |
| Aminoglutethimide | Pegaspargase |
| Anagrelide | Pegfilgrastim |
| Anandron | PEG-INTRON |
| Anastrozole | PEG-L-asparaginase |
| Arabinosylcytosine | Phenylalanine Mustard |
| Ara-C | Platinol |
| Aranesp | Platinol-AQ |
| Aredia | Prednisolone |
| Arimidex | Prednisone |
| Aromasin | Prelone |
| Arsenic trioxide | Procarbazine |
| Asparaginase | PROCRIT |
| ATRA | Proleukin |
| Avastin | Prolifeprospan 20 with Carmustine implant |
| BCG | Purinethol |

TABLE 2-continued

Examples of Chemotherapeutic Agents

| | |
|---|---|
| BCNU | Raloxifene |
| Bevacizumab | Rheumatrex |
| Bexarotene | Rituxan |
| Bicalutamide | Rituximab |
| BiCNU | Roveron-A (interferon alfa-2a) |
| Blenoxane | Rubex |
| Bleomycin | Rubidomycin hydrochloride |
| Bortezomib | Sandostatin |
| Busulfan | Sandostatin LAR |
| Busulfex | Sargramostim |
| C225 | Solu-Cortef |
| Calcium Leucovorin | Solu-Medrol |
| Campath | STI-571 |
| Camptosar | Streptozocin |
| Camptothecin-11 | Tamoxifen |
| Capecitabine | Targretin |
| Carac | TAXOL (Paclitaxel) |
| Carboplatin | Taxotere |
| Carmustine | Temodar |
| Carmustine wafer | Temozolomide |
| Casodex | Teniposide |
| CCNU | TESPA |
| CDDP | Thalidomide |
| CeeNU | Thalomid |
| Cerubidine | TheraCys |
| cetuximab | Thioguanine |
| Chlorambucil | Thioguanine Tabloid |
| Cisplatin | Thiophosphoamide |
| Citrovorum Factor | Thioplex |
| Cladribine | Thiotepa |
| Cortisone | TICE |
| Cosmegen | Toposar |
| CPT-11 | Topotecan |
| Cyclophosphamide | Toremifene |
| Cytadren | Trastuzumab |
| Cytarabine | Tretinoin |
| Cytarabine liposomal | Trexall |
| Cytosar-U | Trisenox |
| Cytoxan | TSPA |
| Dacarbazine | VCR |
| Dactinomycin | Velban |
| Darbepoetin alfa | VELCADE (bortezomib) |
| Daunomycin | VePesid |
| Daunorubicin | Vesanoid |
| Daunorubicin hydrochloride | Viadur |
| | Vinblastine |
| Daunorubicin liposomal | Vinblastine Sulfate |
| DaunoXome | Vincasar Pfs |
| Decadron | Vincristine |
| Delta-Cortef | Vinorelbine |
| Deltasone | Vinorelbine tartrate |
| Denileukin diftitox | VLB |
| DepoCyt | VP-16 |
| Dexamethasone | Vumon |
| Dexamethasone acetate | Xeloda |
| dexamethasone sodium phosphate | Zanosar |
| | Zevalin |
| Dexasone | Zinecard |
| Dexrazoxane | Zoladex |
| DHAD | Zoledronic acid |
| DIC | Zometa |
| Diodex | Gliadel wafer |
| Docetaxel | Glivec |
| Doxil | GM-CSF |
| Doxorubicin | Goserelin |
| Doxorubicin liposomal | granulocyte-colony stimulating factor |
| Droxia | Granulocyte macrophage colony stimulating factor |
| DTIC | |
| DTIC-Dome | Halotestin |
| Duralone | HERCEPTIN (trastuzumab) |
| Efudex | Hexadrol |
| Eligard | Hexalen |
| Ellence | Hexamethylmelamine |
| Eloxatin | HMM |
| Elspar | Hycamtin |
| Emcyt | Hydrea |
| Epirubicin | Hydrocort Acetate |
| Epoctin alfa | Hydrocortisone |
| Erbitux | Hydrocortisone sodium phosphate |
| Erwinia L-asparaginase | Hydrocortisone sodium succinate |
| Estramustine | Hydrocortone phosphate |
| Ethyol | Hydroxyurea |
| Etopophos | Ibritumomab |
| Etoposide | Ibritumomab Tiuxetan |
| Etoposide phosphate | Idamycin |
| Eulexin | Idarubicin |
| Evista | Ifex |
| Exemestane | IFN-alpha |
| Fareston | Ifosfamide |
| Faslodex | IL-2 |
| Femara | IL-11 |
| Filgrastim | Imatinib mesylate |
| Floxuridine | Imidazole Carboxamide |
| Fludara | Interferon alfa |
| Fludarabine | Interferon Alfa-2b (PEG conjugate) |
| Fluoroplex | Interleukin-2 |
| Fluorouracil | Interleukin-11 |
| Fluorouracil (cream) | Intron A (interferon alfa-2b) |
| Fluoxymesterone | Leucovorin |
| Flutamide | Leukeran |
| Folinic Acid | Leukine |
| FUDR | Leuprolide |
| Fulvestrant | Leurocristine |
| G-CSF | Leustatin |
| Gefitinib | Liposomal Ara-C |
| Gemcitabine | Liquid Pred |
| Gemtuzumab ozogamicin | Lomustine |
| Gemzar | L-PAM |
| GLEEVEC (imatinib) | L-Sarcolysin |
| Lupron | Meticorten |
| Lupron Depot | Mitomycin |
| Matulane | Mitomycin-C |
| Maxidex | Mitoxantrone |
| Mechlorethamine | M-Prednisol |
| Mechlorethamine Hydrochlorine | MTC |
| | MTX |
| Medralone | Mustargen |
| Medrol | Mustine |
| Megace | Mutamycin |
| Megestrol | Myleran |
| Megestrol Acetate | IRESSA (gefitinib) |
| Melphalan | Irinotecan |
| Mercaptopurine | Isotretinoin |
| Mesna | Kidrolase |
| Mesnex | Lanacort |
| Methotrexate | L-asparaginase |
| Methotrexate Sodium | LCR |
| Methylprednisolone | |

The subject invention also concerns methods for inhibiting glucose transport in a cell by contacting the cell with an effective amount of a compound, agent, or composition of the invention. In one embodiment, the compound inhibits the activity of a glucose transporter protein. In one embodiment, the cell is a human or mammalian cell, and can be a cancer or tumor cell or other cell that exhibits abnormal proliferation, survival, migration or differentiation. In one embodiment, the cell constitutively expresses or expresses elevated or abnormal levels of a glucose transport protein, such as Glut-1. The agent or compound can be any agent or compound that inhibits one or more glucose transporter (Glut) proteins, or that inhibits expression of a gene or polynucleotide encoding a Glut protein.

The subject invention also concerns methods for treating a person or animal having a disorder associated with constitutive, abnormal, or elevated expression of a glucose transporter protein in a cell, wherein a therapeutically effective amount of a compound, agent, or composition or the invention is administered to the person or animal. The agent or compound can be any agent or compound that inhibits one or more glucose transporter (Glut) proteins, or that inhibits expression of a gene or polynucleotide encoding a Glut protein. The disorder can be one characterized, for example, by abnormal cell proliferation, cell survival, cell migration, and/or cell differentiation. In one embodiment, the compound or agent binds to and inhibits activity of a Glut-1 protein.

Depending upon the disorder or disease condition to be treated, a suitable dose(s) may be that amount that will reduce proliferation or growth of the target cell(s). In the context of cancer, a suitable dose(s) is that which will result in a concentration of the active agent in cancer tissue, such as a malignant tumor, which is known to achieve the desired response. The preferred dosage is the amount which results in maximum inhibition of cancer cell growth, without unmanageable side effects. Administration of a compound and/or agent can be continuous or at distinct intervals, as can be determined by a person of ordinary skill in the art.

To provide for the administration of such dosages for the desired therapeutic treatment, in some embodiments, pharmaceutical compositions of the invention can comprise between about 0.1% and 45%, and especially, 1 and 15%, by weight of the total of one or more of the compounds based on the weight of the total composition including carrier or diluents. Illustratively, dosage levels of the administered active ingredients can be: intravenous, 0.01 to about 20 mg/kg; intraperitoneal, 0.01 to about 100 mg/kg; subcutaneous, 0.01 to about 100 mg/kg; intramuscular, 0.01 to about 100 mg/kg; orally 0.01 to about 200 mg/kg, and preferably about 1 to 100 mg/kg; intranasal instillation, 0.01 to about 20 mg/kg; and aerosol, 0.01 to about 20 mg/kg of animal (body) weight.

The subject invention also concerns kits comprising a composition comprising an inhibitor compound and/or agent of the invention in one or more containers. Kits of the invention can optionally include pharmaceutically acceptable carriers and/or diluents. In one embodiment, a kit of the invention includes one or more other components, adjuncts, or adjuvants as described herein. In another embodiment, a kit includes one or more anti-cancer agents, such as those agents described herein. In one embodiment, a kit of the invention includes instructions or packaging materials that describe how to administer a compound or composition of the kit. Containers of the kit can be of any suitable material, e.g., glass, plastic, metal, etc., and of any suitable size, shape, or configuration. In one embodiment, a compound and/or agent of the invention is provided in the kit as a solid, such as a tablet, pill, or powder form. In another embodiment, a compound and/or agent of the invention is provided in the kit as a liquid or solution. In one embodiment, the kit comprises an ampoule or syringe containing a compound and/or agent of the invention in liquid or solution form.

Mammalian species which benefit from the disclosed methods include, but are not limited to, primates, such as apes, chimpanzees, orangutans, humans, monkeys; domesticated animals (e.g., pets) such as dogs, cats, guinea pigs, hamsters, Vietnamese pot-bellied pigs, rabbits, and ferrets; domesticated farm animals such as cows, buffalo, bison, horses, donkey, swine, sheep, and goats; exotic animals typically found in zoos, such as bear, lions, tigers, panthers, elephants, hippopotamus, rhinoceros, giraffes, antelopes, sloth, gazelles, zebras, wildebeests, prairie dogs, koala bears, kangaroo, opossums, raccoons, pandas, hyena, seals, sea lions, elephant seals, otters, porpoises, dolphins, and whales. Other species that may benefit from the disclosed methods include fish, amphibians, avians, and reptiles. As used herein, the terms "patient" and "subject" are used interchangeably and are intended to include such human and non-human species. Likewise, in vitro methods of the present invention can be carried out on cells of such human and non-human species.

MATERIALS AND METHODS FOR EXAMPLES 1-5

Cell Culture.

Breast carcinoma cell lines MCF-7, T47D, p53 negative osteosarcoma cell line Saos-2 and NSCLC cell line H1299 were grown in Dulbecco's modified Eagle's medium supplemented with 10% fetal bovine serum (PBS). SV40-transformed human lung fibroblast WI-38-VA13 was obtained from ATCC and cultured in Minimal essential medium eagle with Earle's salt and L-glutamine containing 10% FBS, sodium pyruvate, and non-essential amino acids. NSCLC cell lines A549, H358, H226, H1650 were grown in Ham's F12K containing 10% FBS. Human microvascular endothelial cells of lung (HMEC-L) and human aortic endothelial cells (HAEC) were grown in EGM bullet kit medium containing 5% FBS from Clonetics.

Cell Lysate Preparation and Western Blot.

Lysates from cells were prepared by NP40 lyses. Samples were boiled in equal volume of 2×SDS sample buffer, and separated on 8% polyacrylamide gels. After semi-dry transfer to supported nitrocellulose membranes, the blots were probed with monoclonal antibody to Glut-1 from R&D systems. The proteins were detected by using an enhanced chemiluminescence assay system from AMERSHAM BIOSCIENCES.

Immunofluorescence.

Glut-1 monoclonal antibody was purchased from R&D SYSTEMS INC (Minneapolis, Minn.). Cells were plated onto poly-D-lysine (SIGMA) coated 8-well glass chamber slides (10,000 cells per well) for immunostaining. Cells were fixed in 3.5% paraformaldehyde for 25 minutes, permeabilized in 0.2% Triton X-100/PBS for 5 minutes, and blocked in 5% normal goat serum in PBS at room temperature for 1 hour. Primary antibody incubation was performed overnight at 4° C. After washing, secondary antibody incubation was performed with goat anti-mouse IgG Alexa Fluor-488 for 30 minutes at room temperature. DAPI counterstain (4',6-diamidino-2-phenylindole) was detected using VECTASHIELD Mounting Medium with DAPI (VECTOR LABORATORIES, INC.). Control experiments demonstrated that there was no detectable staining by secondary antibodies only (data not shown). Slides were observed by fluorescence microscopy using Leica DM LB2 microscope (40×/0.75 numerical aperture) with a QIMAGING Retiga1300 camera.

MTT Assay.

MTT assays were performed by the following well-established method. In a 96 well tissue culture plate 10000 cells were plated in each well. The cells were incubated in presence or absence of Glut1 antibody for 18 hours. 3-(4,5-climethylthiazol-2-yl)-2,5-diphenyltetrazolium bromide (MTT) was dissolved in PBS (10 mg/ml) and filter sterilized. Three hours before the end of the incubation 20 µl of MTT solution was added to each well containing cells in 96 well plates. The plate was incubated in an incubator at 37° C. for 3 hours. Media was aspirated gently and 200 µl of DMSO was added to each well to dissolve formazan crystals. The absorbance was measured at 550 nm.

Proliferation Assay.

MCF-7, H1299 and H1650 cells were plated onto poly-D-lysine (Sigma) coated 8-well glass chamber slides (10,000 cells per well). The cells were incubated with 0.1 mg/ml Glut-1 monoclonal antibody for 18 hours. The cells were fixed and stained using 5-Bromo-2' deoxyuridine labeling and detection kit from ROCHE according to manufacturer's protocol.

Apoptosis Assay.

MCF-7, H1299 and H1650 cells were plated onto poly-D-lysine (SIGMA) coated 8-well glass chamber slides (10,000 cells per well). The cells incubated with 0.1 mg/ml Glut-1 monoclonal antibody for 18 hours served as controls. The cooperative effect of drugs was evaluated by adding 5 μM of cisplatin or paclitaxel or 10 μM gefitinib. After 18 hours of incubation cells were fixed and stained according to manufacturer's instructions using PROMEGA's DEADEND Colorimetric TUNEL system.

Glucose Uptake Assay.

Cellular glucose uptake was measured by incubating cells in glucose-free RPMI 1640 with 0.2 Ci/mL [$^3$H]2-deoxyglucose (specific activity, 40 Ci/mmol) for 60 minutes. After the cells were washed with ice-cold PBS, the radioactivity in the cell pellets was quantified by liquid scintillation counting.

Statistical Analyses.

Unless other wise specified experiments were done in triplicate. Error bars were generated based on the 95% confidence intervals obtained from these experiments.

Following are examples that illustrate procedures for practicing the invention. These examples should not be construed as limiting. All percentages are by weight and all solvent mixture proportions are by volume unless otherwise noted.

EXAMPLES 1-5

Example 1

Expression Levels of Glut1 in Transformed and Primary Cell Lines

Glut-1 is the most widely expressed isoform of the Glut family that provides cells with their basic glucose requirement. Levels of Glut-1 were examined in various cell lines including NSCLC cell lines A549, H1299, H358, H226 and H1650 as well as primary cell line HMEC-L. MCF-7 and T47D breast cancer cell lines were also evaluated. Jurkats, U937, Saos-2, WI38VA13 and HAEC were analyzed for expression of Glut1 protein by Western blot. As depicted in FIG. 1, H1299, H1650, MCF-7, T47D and Jurkats show comparatively higher expression of Glut-1. At the same time, Glut-1 levels appeared to be low in U937, H226 and A549 cells. Actin levels were comparable across the cell lines, suggesting that observed differences in the levels of Glut-1 are genuine.

Example 2

Effect of Glut-1 Antibody on Cell Proliferation

The ability of monoclonal Glut-1 antibody to affect cell proliferation was assessed. H1299, H1650, T47D and MCF-7 cell lines were incubated in presence of different dilutions of the anti-Glut-1 monoclonal antibody for 18 hours. Similar dilutions of a non-specific IgG1 isotype antibody were used as the control. An MTT assay revealed that 0.1 mg/ml of the antibody was able to repress the proliferation of these cell lines by at least 50% (Data not shown).

Figure 2:
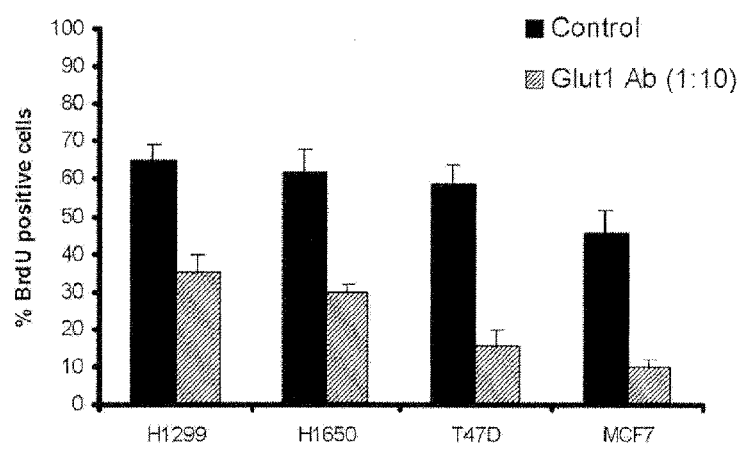
In FIG. 2, H1299, H1650, T47D and MCF-7 cells were grown on poly-D-lysine coated chamber slide in presence or absence of 0.1 mg/ml Glut 1 antibody and BrdU assay was performed. The results show 40-70% decrease in BrdU incorporation in these cell lines.
Figure 3:
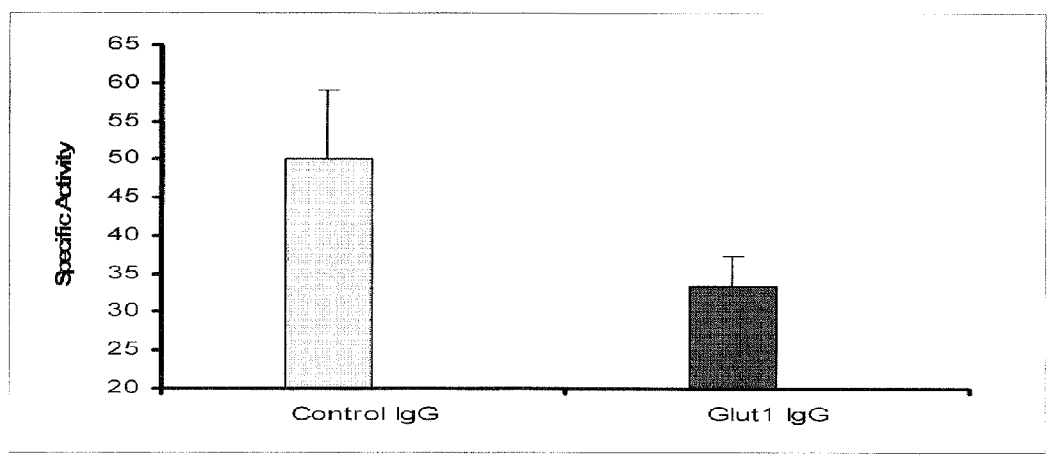
FIG. 3 is a graph showing the results of the glucose uptake assay showing MDA MB treated with an Anti-Glut 1 antibody. Results of the glucose uptake assay in MDA-MB 231 cells treated with an anti-Glut1 antibody for 72 hours. Error bars were generated from two independent experiments. Treatment with Glut1 antibody demonstrates an inhibition of glucose uptake in comparison to a control IgG1 antibody.
Figure 4A:
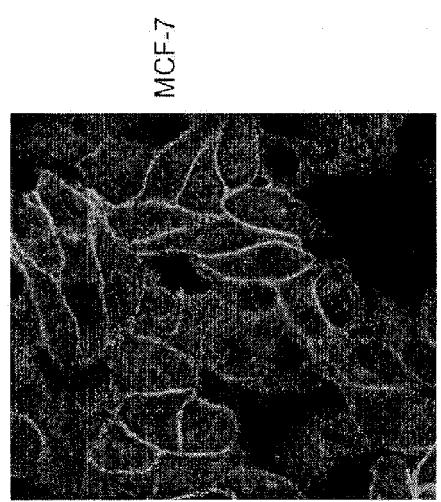
FIGS. 4A-4D—Compared to Breast Cancer Cell lines MCF-7 (FIG. 4B), T47D (FIG. 4C), and MDAMB231 (FIG. 4D), primary breast cell line MCF10A (FIG. 4A) shows less cytoplasmic Glut-1 levels. Additionally, immunostaining reveals the predominantly membranous localization of the Glut-1 receptor is demonstrated in the breast cancer cell lines.
Figure 4B:
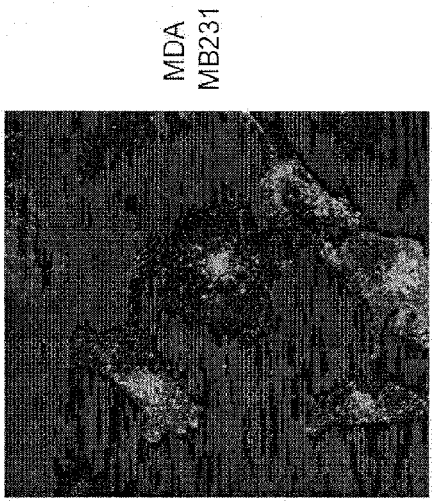
Figure 4C:
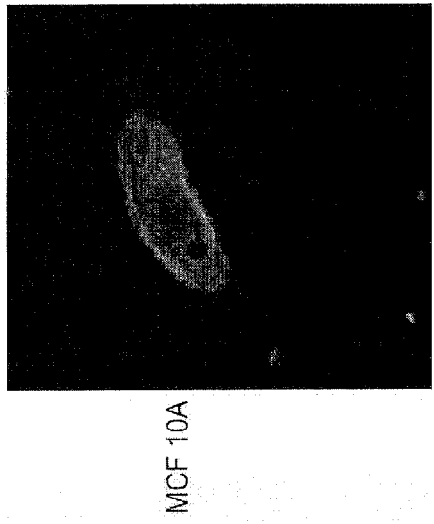
Figure 4D:
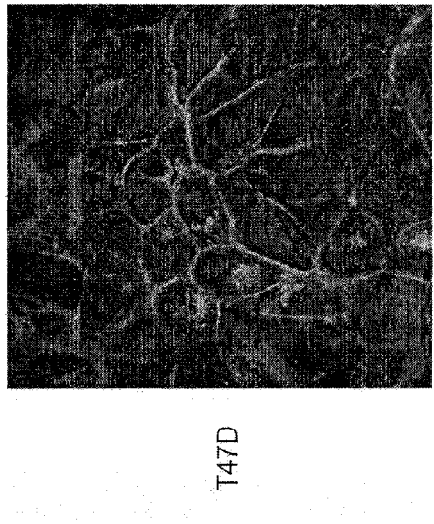

These results were further confirmed by BrdU proliferation assay. H1299, H1650, T47D and MCF-7 Cells were cultured on an eight-well chamber slides and incubated with 0.1 mg/ml monoclonal Glut-1 antibody for 18 hours. A concentration of 0.1 mg/ml IgG1 antibody was used as control. As shown in FIG. 2, the treatment with the Glut-1 antibody led to a 45-70% decrease in the proliferation of all the four cell lines tested, suggesting that incubation with this antibody can inhibit cell proliferation.

Example 3

Localization of Glut1 Receptor

An immunofluorescence experiment was performed to confirm the ability of antibody to bind the Glut-1 receptor. MCF-7 and F11650 cells were plated on chamber slides. After washing the cells were fixed and immunostained with the Glut-1 monoclonal antibody. The cells were then visualized with secondary antibody conjugated to Alexafluor-488. As shown in FIGS. 4A-4D, staining for Glut-1 is visible in the cytoplasm and confocal microscopy confirmed the localization of the Glut-1 transporter to the cell membrane. This suggests that transporter is present on the cell surface and implies that anti-Glut-1 antibody prevents cell proliferation by altering Glut-1 transporter's function, presumably by inducing conformational changes in Glut-1 transporter function. The MDAMB231 breast cancer cell line demonstrates a 10% to 50% reduction in glucose uptake when incubated with the anti-Glut 1 antibody. This reduction of glucose uptake may be enough to reduce proliferation and induce apoptosis in aggressive cancer cell lines who require high levels of glucose to meet their energy needs.

Additionally, by immunostaining the predominantly membranous localization of the Glut-1 receptor is demonstrated in the breast cancer cell lines in comparison to the primary breast cell line MCF10A, which is particularly evident in the MCF7 and T47D cell lines (FIGS. 4A-4D).

Example 4

Glut-1 Enhances the Inhibition of Cell Proliferation by Chemotherapeutic Drugs

Figure 5A:
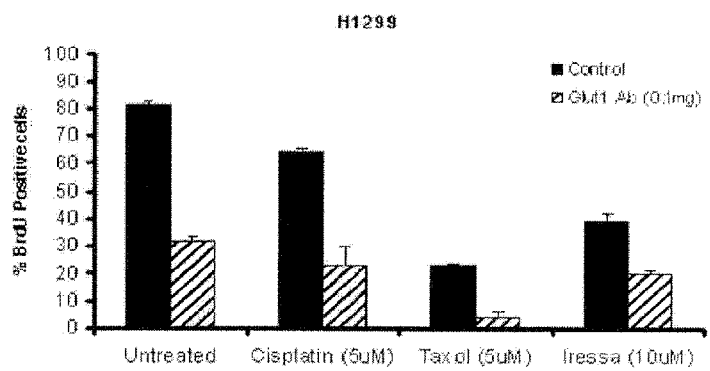
FIGS. 5A-5C show the combined effect of chemotherapeutic drugs and Glut-1 antibody on cell proliferation. H1299 (FIG. 5A), H1650 (FIG. 5B), and MCF-7 (FIG. 5C) cells were grown on chamber slides as described above and treated either with cisplatin, paclitaxel or iressa in presence or absence of Glut-1 antibody (0.1 mg) for 18 hours. The proliferation was measured by BrdU incorporation. The results show that combination of chemotherapeutic drugs with the Glut-1 antibody further diminishes the cell proliferation.
Figure 5B:
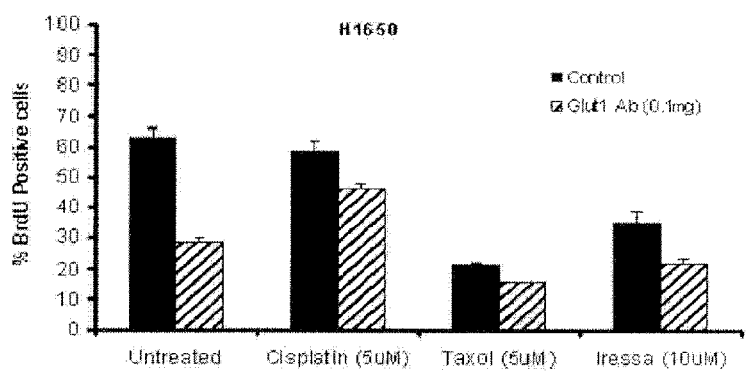
Figure 5C:
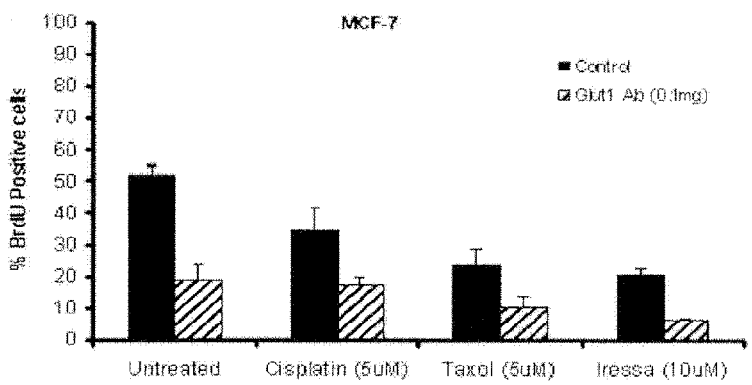

Experiments were done to evaluate whether anti-Glut-1 antibody could synergize with standard chemotherapeutic agents to inhibit proliferation of H1299, H1650 and MCF-7. The cells were plated on chamber slides and incubated in presence of chemotherapeutic agents (5 μM cisplatin, 5 μM paclitaxel or 10 μM geftinib) in absence or presence of 0.1 mg/ml anti-Glut-1 antibody. The treatment with drugs led to significant decrease in proliferation of all the three cancer cell lines. Addition of Glut-1 antibody led to a greater reduction in cell proliferation in NSCLC cell lines H1299 and H1650, and breast cancer cell line MCF7 (FIGS. 5A-5C). In the H1299 line treatment with the anti-Glut-1 antibody alone inhibited proliferation by 62%; when added to cisplatin it enhanced cisplatin induced inhibition of proliferation by 62%, paclitaxel by 74% and gefitinib by 42%. Similarly in the H1650 cell line treatment with anti-Glut-1 antibody alone inhibited proliferation by 55%; when added to cisplatin, it enhanced cisplatin induced inhibition of proliferation by 18%; paclitaxel by 23% and gefitinib by 46%. In the MCF7 cell line, anti-Glut-I antibody alone inhibited proliferation by 59%, when added to cisplatin it enhanced cisplatin-induced inhibition of proliferation by 40%, paclitaxel by 47% and gefitinib by 59%. The results are shown in FIGS. 5A-5C.

Example 5

Glut-1 Enhances the Apoptosis by Chemotherapeutic Drugs

Figure 6A:
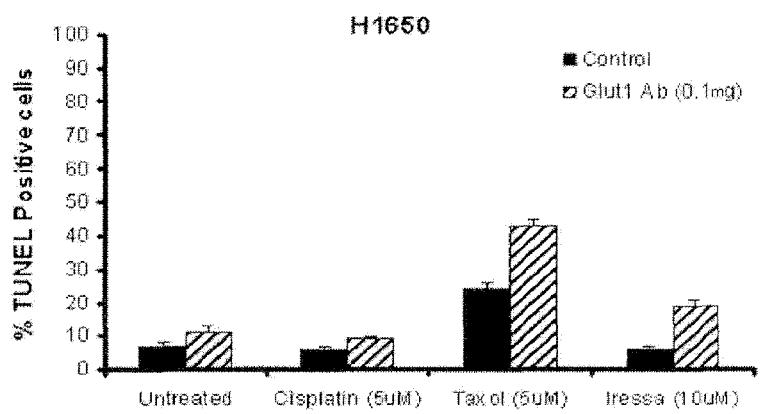
FIGS. 6A-6C show the combined effect of chemotherapeutic drugs and Glut-1 antibody on cell apoptosis. H1650 (FIG. 6A), H1299 (FIG. 6B), and MCF-7 (FIG. 6C) cells were grown on chamber slides as described above and treated either with cisplatin, paclitaxel or iressa in presence or absence of Glut-1 antibody (0.1 mg) for 18 hours. The apoptosis was measured by TUNEL assay. The results demonstrate that the combination of chemotherapeutic drugs with the Glut-1 antibody results in additive effect on cell apoptosis.
Figure 6B:
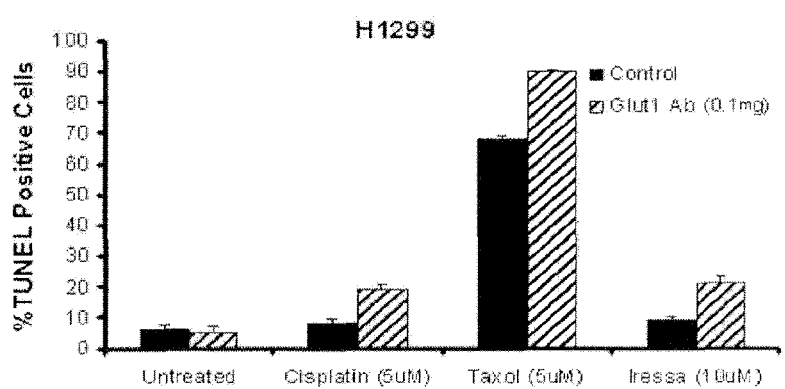
Figure 6C:
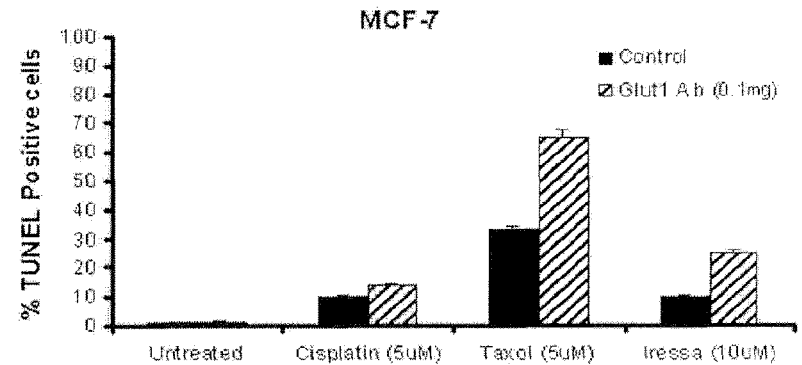

Since the above drugs are known to be strong inducers of apoptosis, attempts were made to assess whether anti-Glut-1 antibody synergizes with them to induce apoptosis. NSCLC cell lines, H1299 and H1650, and breast cancer cell line, MCF7 were evaluated for apoptosis by the TUNEL assay, after treatment with 5 µM cisplatin, 5 µM paclitaxel or 10 µM geftinib alone, or with anti-Glut-1 antibodies. Glut-1 antibodies enhanced the apoptotic effects of cisplatin, paclitaxel and gefitinib (FIGS. 6A-6C) in H1650 cell line by 43%, 62% and 111%; in H1299 by 111%, 30% and 71% and in MCF7 cell line by 37%, 91% and 133%, respectively.

Figures 7A, 7B:
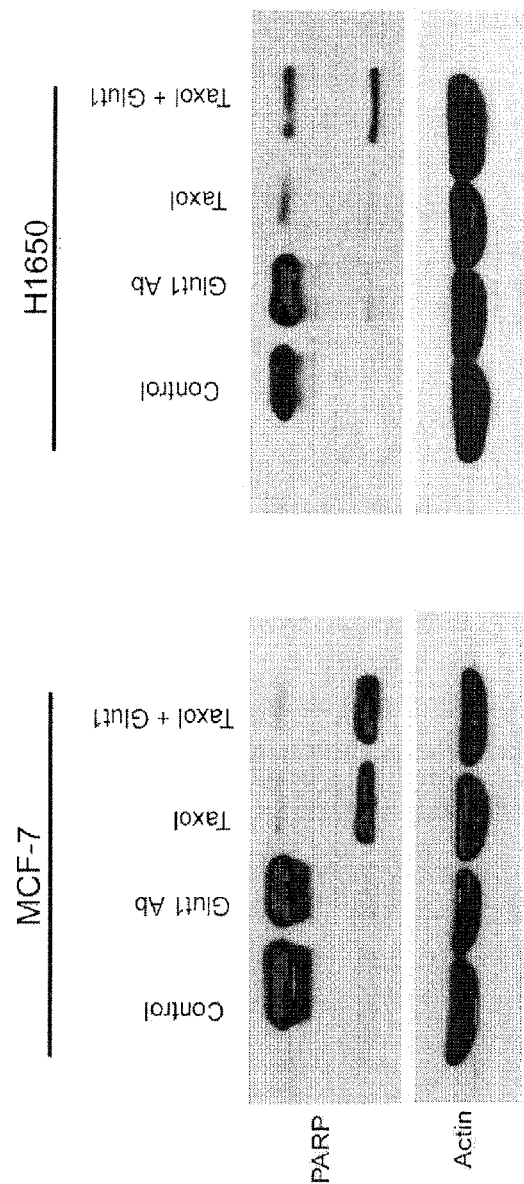
FIGS. 7A and 7B are blots comparing the effect of Paclitaxel in the presence or absence of Glut 1 antibody. MCF-7 (FIG. 7A) and H1650 (FIG. 7B) cells were treated with 20 µM Paclitaxel in presence or absence of Glut1 antibody for 18 hours. Apoptosis was assessed using PARP cleavage. Combined treatment of cells with Paclitaxel and Glut1 antibody leads to more potent apoptotic stimuli in comparison to Paclitaxel alone.
Figure 8:
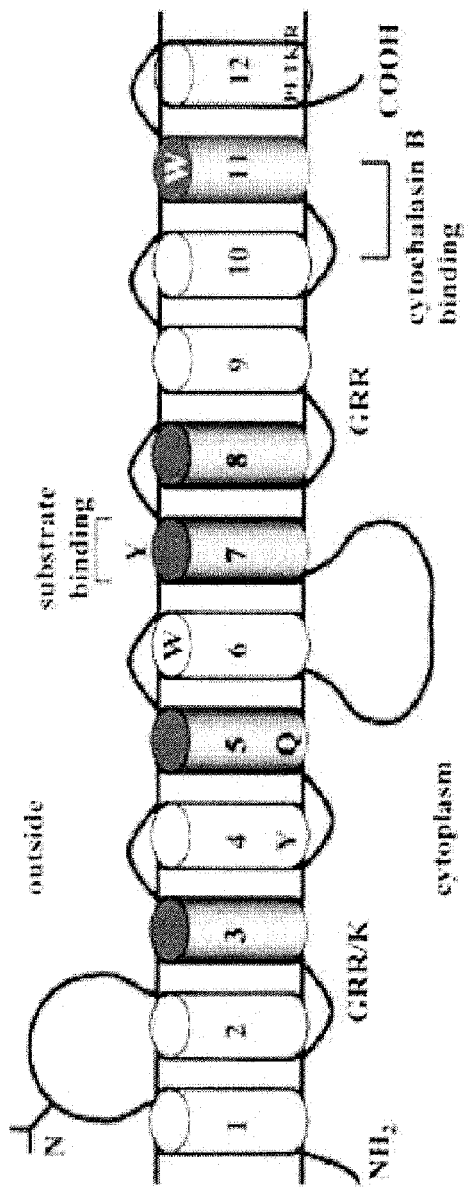
FIG. 8 is a diagram of membrane-bound glucose transporters.
Figure 9:
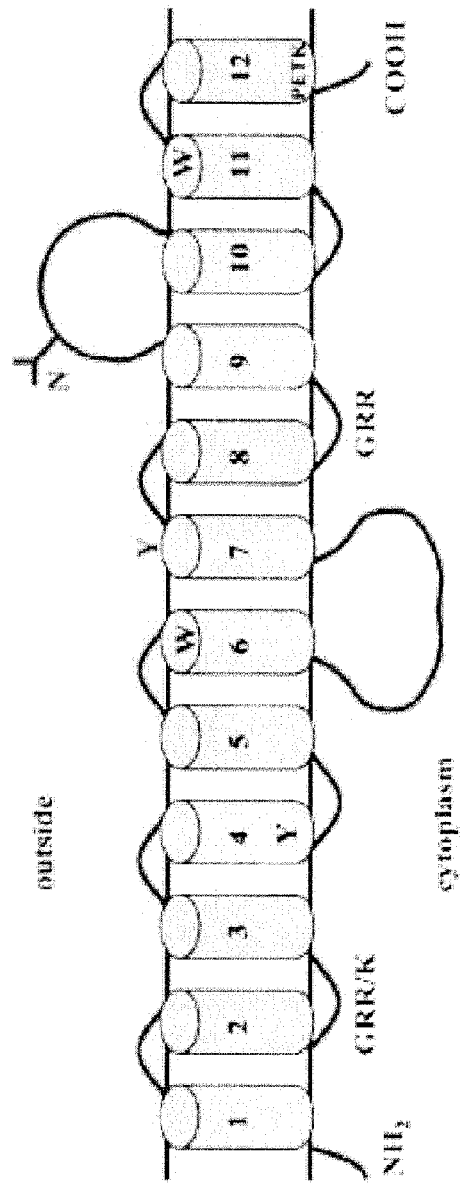
FIG. 9 is a diagram of membrane-bound glucose transporters.
Figure 10:
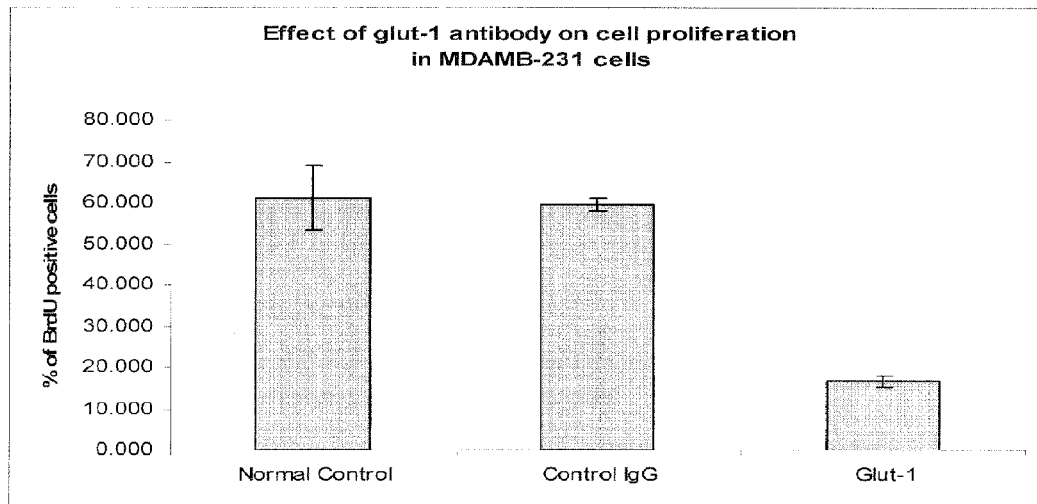
FIG. 10 is a graph showing the effect of glut-1 antibody on cell proliferation in MDAMB-231 cells.
Figure 11:
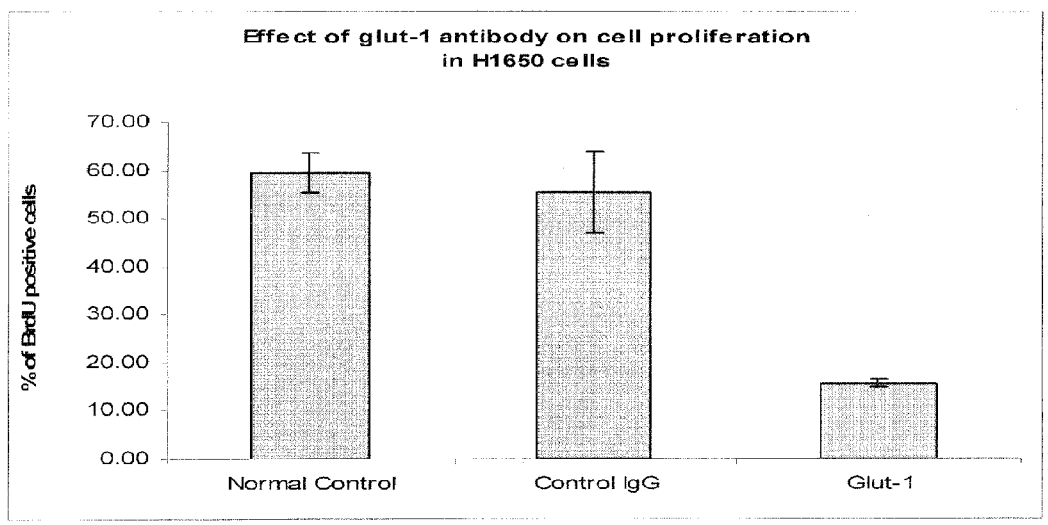
FIG. 11 is a graph showing the effect of glut-1 antibody on cell proliferation in 1650 cells.
Figure 12:
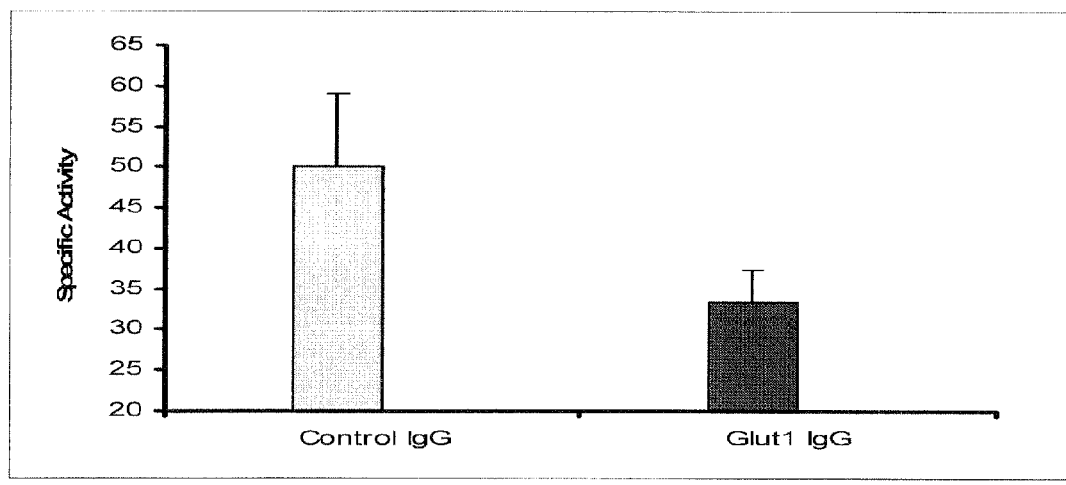
FIG. 12 is a graph showing glucose uptake inhibition in MDAMB-231 cells.
Figure 13:
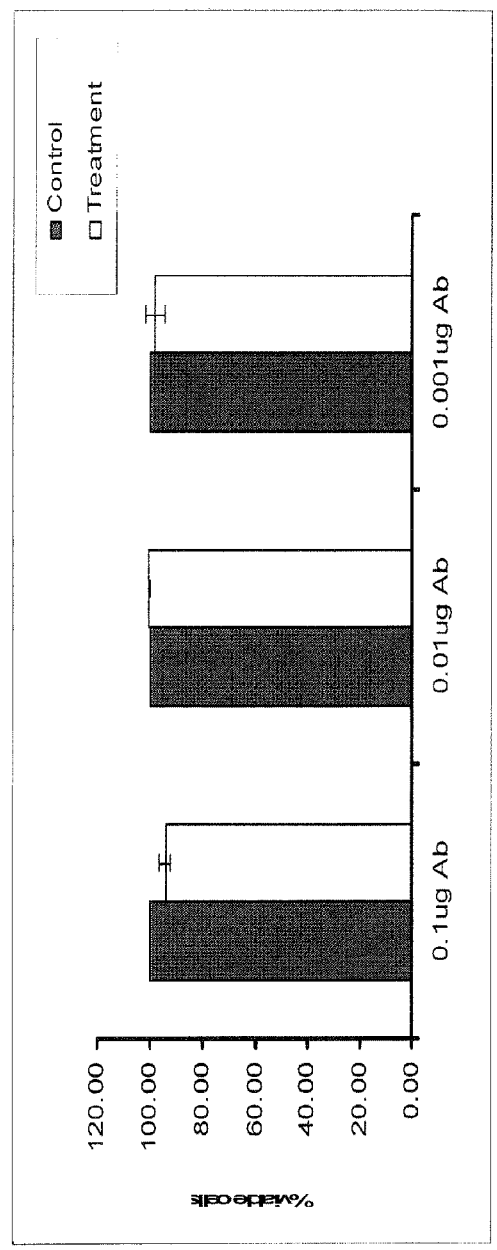
FIG. 13 is a graph showing glucose uptake in Glut-1 negative A549 cell lines.
Figures 14A, 14B, 14C:
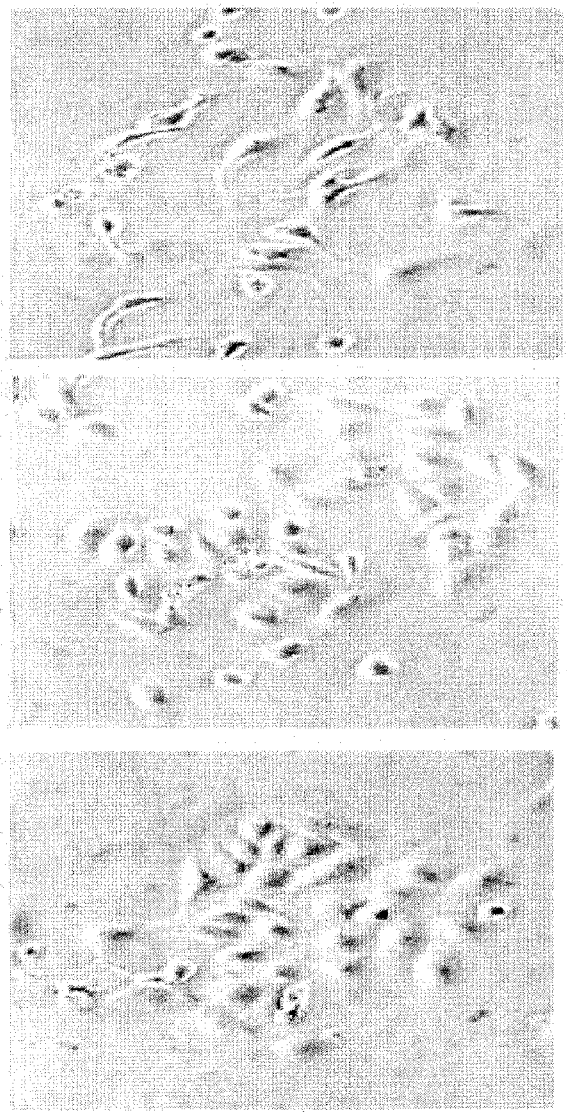
FIGS. 14A-14C are photographs showing the decrease in proliferation of MDAMB-231 cells due to antiglut-1 antibody.
Figures 15A, 15B, 15C:
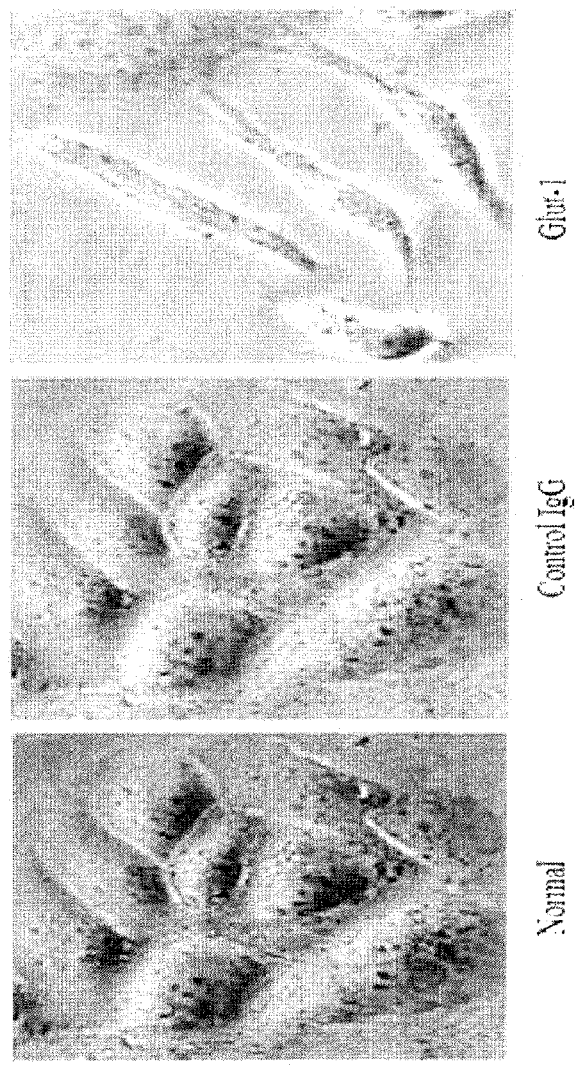
FIGS. 15A-15C are photographs of MDAMB-231 cells showing the decrease in proliferation in a close up view.
Figure 16:
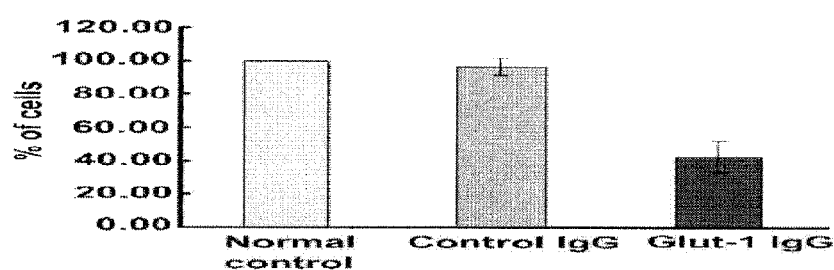
FIG. 16 is a graph of Glut-I antibody invasion inhibition in MDAMB-231 cell lines.

Induction of apoptosis was assessed by measuring PARP cleavage. PARP cleavage was assessed by western blotting of lysates from MCF7 and H1650 cells treated with paclitaxel alone or after co-incubation with 0.1 mg/ml of anti-Glut 1 antibody for 18 hours. Results of these experiments demonstrate that the combined treatment of cells with paclitaxel and Glut1 antibody lead to enhanced apoptosis in comparison to paclitaxel alone (FIGS. 7A and 7B).

Anti-Glut-1 antibodies inhibit proliferation and induce apoptosis in the evaluated NSCLC cell lines and breast cancer cell lines providing evidence that the use of antibodies to Glut-1 may be a viable but an as yet unexplored therapeutic strategy in tumors that over express Glut-1 and consequently demonstrate increased glucose uptake in FDG-PET.

MATERIALS AND METHODS FOR EXAMPLES 6-10

Cell Culture and Treatment.

Breast Cancer line MDAMB-231 and mesothelioma cell line H2052 cells were cultured in DMEM and RPMI (Mediatech, Manassas Va.) containing 10% FBS. Cells were treated in 2.5% serum containing media with anti-Glut-1 antibody twice a day (ALPHA DIAGNOSTIC INTERNATIONAL, INC San Antonio, Tex. (polyclonal) and SPRING BIOSCIENCE, Fremont Calif. (monoclonal)) for 72 hours at a dose of 10 ug/ml. LY294002 compound (SIGMA CHEMICAL CO, St. Louis, Mo.) and Compound C(CALBIOCHEM, Gibbstown, N.J.) was treated at dose of 10 µM and 20 µM respectively.

Tunnel Assay.

TUNEL assay was performed on the fixed cells using DEAD END COLORIMETRIC TUNEL system (PROMEGA BIOSCIENCES INC, San Luis Obispo, Calif.). Cells were plated in poly-D-lysine coated chamber slides at a density of 3,000 cells per well and then treated with anti-Glut-1 antibody and or LY294002 or compound C for 72 hours. Tunnel positive cells were visualized by microscopy and quantitated by counting 4 fields of 100 cells in quadruplicate. Data are presented as the percentage of tunnel positive cells out of the 100 cells counted.

Cell Growth Inhibition Assay.

To determine the inhibitory effect of anti-Glut-1 antibody in presence and or absence of drug on cell growth a 3-(4,5-dimethylthiazol-2-yl)-2,5-diphenyltetrazolium bromide (MIT) assay will be used. Cells will be plated in 96-well plates and then cultured in medium with or without anti-Glut-1 antibody and after the treatment the percentage of viable cells in each well will be examined by MIT assay using spectrophotometer.

Lysate Preparation and Western Blotting.

Lysates from cells treated with anti-Glut-1 antibody and LY294002 were prepared by NP-40 lysis as described earlier and 100 ug protein was run on polyacrylamide-SDS gel and then immunoblotted with antibodies to pAKT, total AKT, AMPKα, total AMPKα, pBad, Bclxl, PTEN, PARP, Caspase-3,β-catenin, fibronectin, vimentin, total caspase-9, surviving, XIAP and Actin. Antibodies to pAKT, total AKT, AMPKα, total AMPKα, pBad, Bclxl, PTEN, PARP, and Caspase-3 antibody were obtained from CELL SIGNALING TECHNOLOGY INC, Danvers Mass. β-catenin, fibronectin, Vimentin, total caspase-9, and survivin were purchased from SANTA CRUZ BIOTECHNOLOGY, Santa Cruz Calif. XIAP antibody is obtained from STRESSGEN BIOREAGENTS CORPORATION, Victoria, BC. Antibody to Actin was purchased from SIGMA CHEMICAL CO, St Louis Mo.

ATP Assay.

ATP assay was performed according to manufacturer protocol of ENLITEN ATP assay system bioluminescence detection kit. Briefly, 3000 cells/well were plated in 12 well plates and treated with antiglut-1 antibody for 72 hours. Following treatment, the cellular ATP was extracted (Yang N-C et al., 2002) by adding 1 ml of boiling water and cell suspension was made by repeated pipetting. Suspension of the cells was then transferred into a microcentrifuge tube for centrifugation (12,000 g for 5 minutes at 4° C.) and 10 µl of the supernatent was used for bioluminescence measurement in turner biosystems 20/20° luminometer. The standard curve of ATP was obtained by serial dilution of 7 µM ATP solution.

Transient Transfection with Small Interfering RNAs.

For the transient transfection with small interfering RNAs (siRNA), cells were plated in six-well plates. Glut-1 siRNA (SIGMA CHEMICAL CO, St Louis, Mo.) or control siRNA (SANTA CRUZ BIOTECHNOLOGY, Santa Cruz, Calif.) was transfected with Oligofectamine reagent (INVITROGEN) according to the manufacturer's instructions. Transfected cells were used for ATP assay and Western blot analysis.

Migration Assay.

The protective effect of anti-Glut-1 antibody on invasive ability of MDA-MB-231 cells was assayed according to the method reported before (Vukanovic et al., 1993; Dasgupta et al., 2006; Gazdar et al., 2003). Briefly, the upper surface of the filters was precoated with collagen (100 µg/filter). Matrigel was applied to the upper surface of the filters (50 µg/filter) and dried in a hood. These filters were placed in Boyden chambers. Cells were grown separately and treated with anti-Glut-1 antibody for 72 hours. Following treatment, cells were trypsinized and 5000 cells were plated in the upper chamber of the filter in media containing 0.1% bovine serum albumin (SIGMA CHEMICAL CO, St Louis, Mo.). Media containing 20% fetal bovine serum was placed in the lower well as an attractant and the chambers were incubated at 37° C. for 18 hours. Non-migrating cells on the upper surface of the filters were removed after 18 hours by wiping with cotton swabs. The filters were processed first by fixing in methanol followed by staining with hematoxylin. The cells migrating on the other side of the filters were quantitated by counting three different fields under 40× magnification.

EXAMPLES 6-10

Example 6

Anti-Glut-1 Antibody Induces Apoptosis in MDA-Mb-231 Cells

Figure 18B:
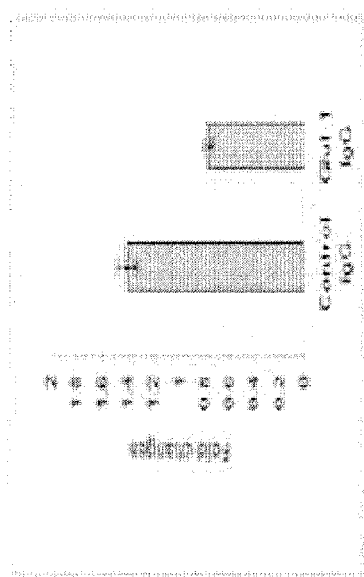
FIGS. 18A and 18B show that treatment with anti-glut-1 antibody decreases Glut-1 protein expression as demonstrated by western blot (FIG. 18A) and Glut-1 mRNA expression as demonstrated by RT-PCR (FIG. 18B).
Figure 18A:
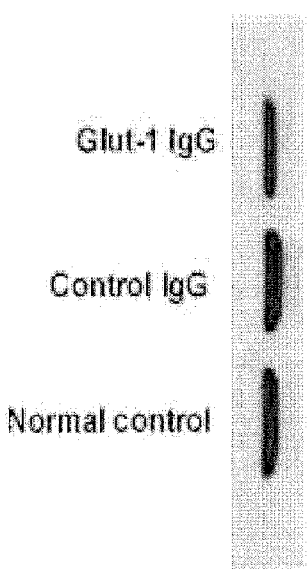

In FIGS. 17A-1, 17A-2, and 17B-17D, it is shown that MDA-MB-231 cells undergo apoptosis when treated with anti-Glut-1 antibody administered twice daily. Optimal apoptosis was seen after 72 hours, when compared to the control IgG-1 antibody (FIG. 17B). Therefore, twice a day instillation of anti-Glut-1 antibody for 72 hours was selected for further experimentation. Apoptosis is demonstrated by PARP cleavage, decrease in total caspases 3 and 9 and cleavage of caspase 3 (FIG. 17D). Treatment with anti-Glut-1 antibody also leads to a downregulation of the Glut-1 transporter protein and mRNA. This is highlighted in FIGS. 18A and 18B.

Example 7

Anti-Glut-1 Antibody Induces Apoptosis Through an Akt Dependent Mechanism

Figure 19:
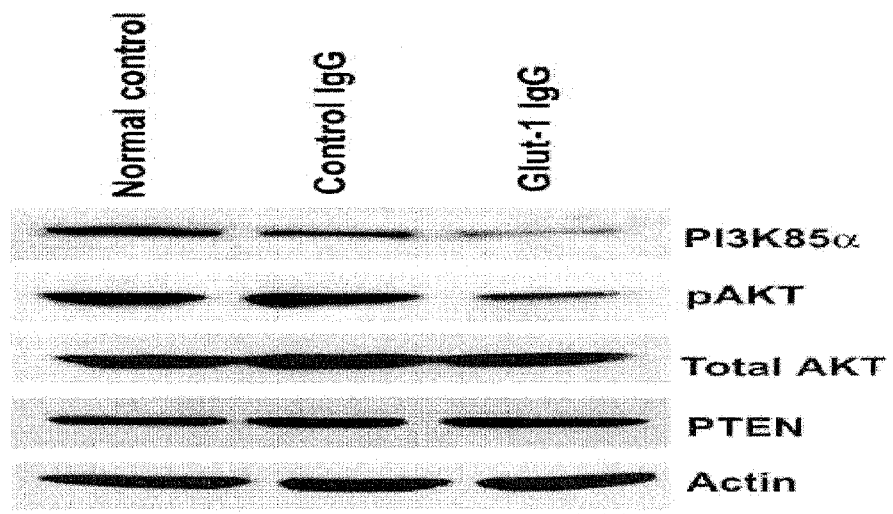
FIG. 19 shows that treatment with anti-Glut-1 antibody decreases the protein expression of 85α subunit of PI3Kinase, and pAkt, without changing total Akt and PTEN levels.

In FIG. 19, it is shown that treatment with the Glut-1 antibody decreases the expression of PI3-kinase (phosphoinositide 3-kinases) and phosphorylated Akt (pAKT). There is no change in total Akt and PTEN (phosphatase and tensin homolog) protein expression (FIG. 19). Apoptosis induced by the anti-Glut-1 antibody is partially reversed by co-treatment with PI3-kinase inhibitor, LY29002, suggesting that the apoptosis induced by anti-Glut-1 antibody is mediated through an Akt dependent mechanism, since Aid is downstream of PI3-Kinase.

Example 8

Figure 20A:
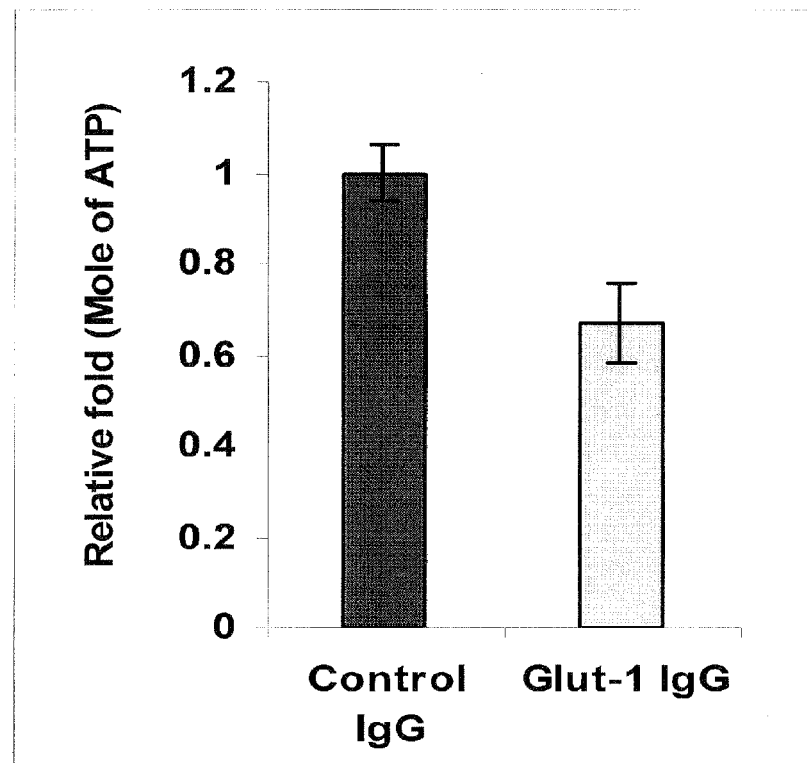
FIGS. 20A and 20B show that treatment with Glut-1 antibody decreases generation of ATP (FIG. 20A) and increases pAMPK (FIG. 20B).
Figure 20B:

Treatment with Anti-Glut-1 Antibody Leads to Decreased Intracellular Levels of ATP and Increases Phosphorylation of AMP Kinase After treatment with anti-glut-1 antibodies, intracellular levels of ATP are decreased in comparison to treatment with control antibodies (FIG. 20A). It is postulated that treatment with anti-glut-1 antibody decreases the entry of glucose in to the cell, presumably by inducing a conformational change in the structure of the glucose transporter. In FIG. 20B, it is shown that treatment with anti-glut-1 antibodies increases the phosphorylation of the pro-apoptotic protein AMP kinase (5'AMP-activated protein kinase). Therefore anti-glut-1 antibodies promote apoptosis by down-regulating the activity of anti-apoptotic protein Akt and by upregulating the pro-apoptotic protein AMP kinase.

Example 9

Figure 21A:
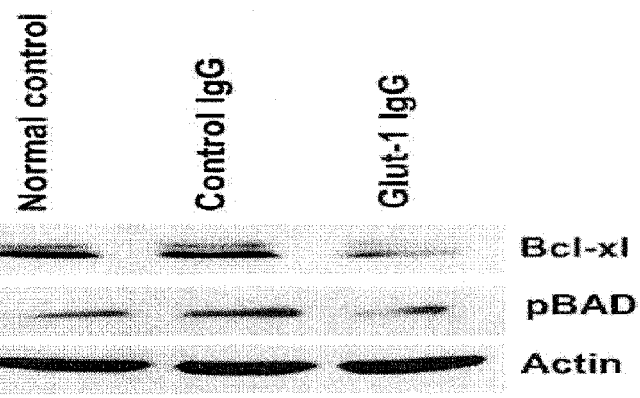
FIGS. 21A and 21B show that treatment with anti-Glut-1 antibody decreases the protein expression of anti-apoptotic proteins Bcl-xl and pBAD (FIG. 21A) and pro-survival proteins XIAP and survivin (FIG. 21B).
Figure 21B:
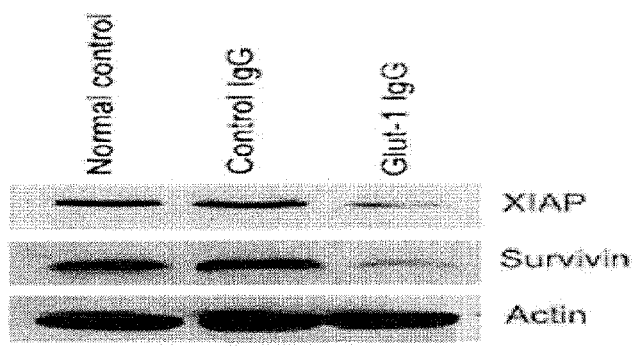

Anti-Glut-1 Antibody Treatment Down Regulates the Expression of Pro-Survival Proteins, XIAP and Survivin In FIG. 21A, it is shown that the protein expression of anti-apoptotic proteins Bcl-xl and pBad are downregulated after treatment with anti-Glut-1 antibodies. This is accompanied by a downregulation of pro-survival proteins XIAP and survivin (FIG. 21B). Decreasing the protein levels of Bcl-xl and pBad and XIAP and survivin may make the cells vulnerable to treatment with chemotherapy, hormonal and targeted agents. This may partially explain why apoptosis induced by chemotherapy, hormonal and targeted agents is enhanced when these agents are co-treated with anti-Glut-1 antibody, as shown in earlier examples.

Example 10

Figure 22A:
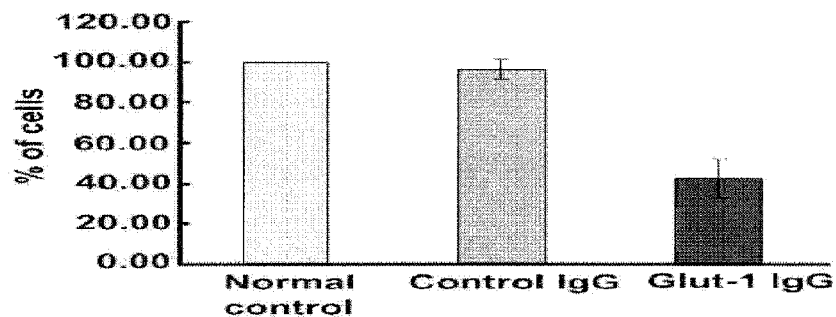
FIGS. 22A and 22B show that treatment with anti-Glut-1 antibody decreases the ability of the treated MDA-MB-231 cells to invade or migrate (FIG. 22A). Decreased expression of mesenchymal phase proteins fibronectin, focal adhesion kinase (FAK) and vimentin in the anti-Glut-1 treated MDA-MB cells indicate decreased transition to the mesenchymal phase where the cells are less vulnerable to treatments with chemotherapy and epidermal growth factor-tyrosine kinase inhibitors (FIG. 22B). The expression of epithelial phase protein β-catenin is unchanged.
Figure 22B:
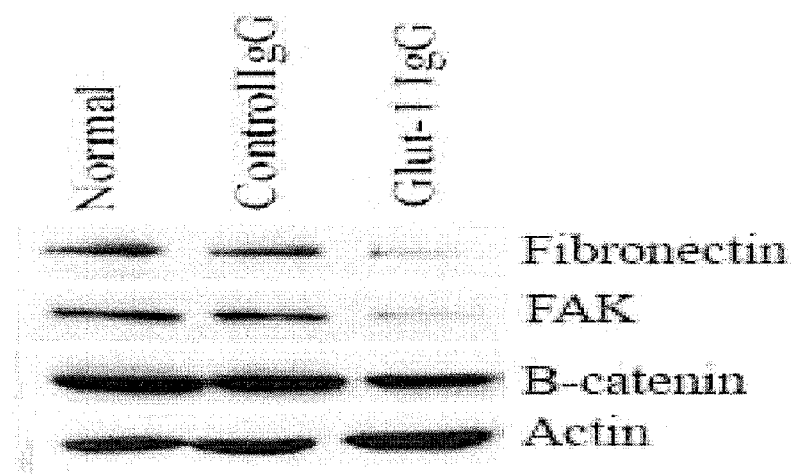

Anti-Glut-1 Antibodies Decrease the Malignant Potential of the Treated Cell Lines by Decreasing its Ability to Migrate and Preventing its Transition in to the Mesenchymal Phase In FIG. 22A, it is shown that treating MDA-MB-231 cells with anti-glut-1 antibody decreases its ability to migrate. In the in vivo system, this presumably will decrease the ability of the cancer cells to migrate. Additionally, in FIG. 22B it is shown that the expression of mesenchymal phase proteins, fibronectin, and focal adhesion kinase are decreased after treatment with the anti-glut-1 antibody. No change in the expression of epithelial protein β-catenin and e-cadherin was observed. This suggests that treatment with anti-glut-1 antibody prevents transition in to the mesenchymal phase where cells are resistant to treatment with chemotherapy and agents targeted to the epidermal growth factor receptor tyrosine kinase inhibitors.

Example 11

Bioenergetics
Mass=Energy=Mass
Cut Off the Energy supply to tumors and you don't have tumor mass
Cut off the Blood Supply—anti-angiogenesis
Reduce Access to Glucose.
Increasing Tumor Mass
→Hypoxia→Anerobic Glycolysis→Aerobic Glycolysis which is facilitated by the up-regulation of high affinity glucose transporters, i.e. Glut-1
Membrane Bound Glucose transporters: Gluts.
Glut 1 Antibodies: A Novel Therapeutic Approach
Membranous localization of Glut-1
Anti-Glut-1 Ab decreases proliferation in MDAMB-231 cells.
Anti-Glut-1 Ab decreases proliferation in H1650 cells.
Glut-1 inhibits glucose uptake in MDAMB-231 cells
Glucose uptake is not inhibited in Glut-1 Negative A549 cell lines.
Glut-1 Ab decreases proliferation in MDAMB-231 cells.
Decreased Percentage of Viable cells as measured by MTT assay in the Glut-1 treated cells.
Invasion Assay: Glut-1 Ab inhibits invasion in MDAMB-231 cell lines.
Anti-Glut-1 antibody augments the decrease in proliferation induced by chemotherapy and gefitinib.
Anti-Glut-1 antibody augments the increase in apoptosis induced by chemotherapy and gefitinib.
Glut-1 increases apoptosis induced by Taxol in MCF-1 and H1650 cells.

All patents, patent applications, provisional applications, and publications referred to or cited herein are incorporated by reference in their entirety, including all figures and tables, to the extent they are not inconsistent with the explicit teachings of this specification.

It should be understood that the examples and embodiments described herein are for illustrative purposes only and that various modifications or changes in light thereof will be suggested to persons skilled in the art and are to be included within the spirit and purview of this application and the scope of the appended claims. In addition, any elements or limitations of any invention or embodiment thereof disclosed herein can be combined with any and/or all other elements or limitations (individually or in any combination) or any other invention or embodiment thereof disclosed herein, and all such combinations are contemplated with the scope of the invention without limitation thereto.

REFERENCES

U.S. Pat. No. 4,559,157
U.S. Pat. No. 4,608,392
U.S. Pat. No. 4,816,567

U.S. Pat. No. 4,820,508
U.S. Pat. No. 4,938,949
U.S. Pat. No. 4,992,478
U.S. Pat. No. 5,167,649
U.S. Pat. No. 5,225,539
U.S. Pat. No. 5,270,163
U.S. Pat. No. 5,411,749
U.S. Pat. No. 5,475,096
U.S. Pat. No. 5,567,588
U.S. Pat. No. 5,580,737
U.S. Pat. No. 5,707,796
U.S. Pat. No. 5,763,177
U.S. Pat. No. 5,840,867
U.S. Pat. No. 6,011,577
U.S. published application US 2004/0002106
PCT publication WO 91/00906
PCT publication WO 91/10741
PCT publication WO 92/01047
PCT publication WO 92/03917
PCT publication WO 92/03918
PCT publication WO 93/05796
PCT publication WO 93/12227
PCT publication WO 94/04667
PCT publication WO 94/25585
PCT publication WO 95/17085
PCT publication WO 96/07754
Barbas et al. *Proc. Nat'l Acad. Sci. USA* 89:4457-4461, 1992
Beidler et al., *J. Immunol.* 141:4053-4060, 1988
Better et al., *Science* 240:1041-1043, 1988
Bird et al. *Science* 242:423-426, 1988
Breaker, R. R. and Joyce, G. (1994) *Chemistry and Biology*, 1:223-229
Breaker, R. R. and Joyce, G. (1995) *Chemistry and Biology*, 2:655-660
Bruggeman et al. (1991) *Eur. J. Immunol.* 21:1323-1326
Bruggeman et al. *Year Immunol.* 7:33-40, 1993
Carmi, N. et al. (1996) *Chemistry and Biology*, 3:1039-1046
Chiu et al., *Mot Cell.*, 10:549-561 (2002)
Choi et al. *Nature Genet.* 4:117-123, 1993
Clavo A C, Brown R S, Wahl R L. Fluorodeoxyglucose uptake in human cancer cell lines is increased by hypoxia. J Nucl Med 1995; 36: 1625-32.
Dasgupta, P.; Kinkade, R.; Joshi, B.; Decook, C.; Haura, E.; Cheliappan, S. Nicotine inhibits apoptosis induced by chemotherapeutic drugs by up-regulating XIAP and survivin. *Proc Natl Acad Sci USA* 2006, 103, (16), 6332-7.
Elbashir et al., *Nature* 411:494-498 (2001)
Gazdar, A. F. Environmental tobacco smoke, carcinogenesis, and angiogenesis: a double whammy? *Cancer Cell* 2003, 4, (3), 159-60.
Green, L. L. et al. *Nature Genet.* 7:13-21, 1994
Griffiths et al. *EMBO J.* 12:725-734, 1993
Harlow and Lane, (1988) Antibodies: A Laboratory Manual ed., Cold Spring Harbor Press
Huston et al., *Proc. Natl. Acad. Sci. USA* 85:5879-5883, 1988
Hutvagner and Zaxnore, *Curr. Opin. Genet. Dev.*, 12:225-232 (2002)
Jones et al., *Nature* 321:552-525, 1986
Kamel-Reid et al. *Science* 242:1706, 1988
Lee et al., *Nature Biotechnol.* 20:500-505 (2002)
Liu et al., (1987a) *J. Immunol.* 139:3521-3526
Liu et al., (1987b) *PNAS* 84:3439-3443
Lonberg, N. et al. *Nature* 368:856-859, 1994
Marks et al. *J. Mol. Biol.* 222:581-597, 1991
McCune et al. *Science* 241:1632-1639, 1988
McManus et al., *RNA* 8:842-850 (2002)
Morrison, S. L. et al. *Proc. Natl. Acad. Sci. USA* 81:6851-6855, 1994
Morrison, S. L., *Science* 229:1202-1207, 1985
Nishimura et al., *Canc. Res.* 47:999-1005, 1987
Oi et al., *BioTechniques* 4:214, 1986
Paddison et al., *Genes Dev.* 16:948-958 (2002)
Paul et al., *Nature Biotechnol.* 20:505-508 (2002)
Santoro, S. W. et al. (1997) *Proc. Natl. Acad. Sci. USA*, 94(9):4262-4266
Sharp, *Genes Dev.*, 15:485-490 (2001)
Shaw et al., *J. Natl. Cancer Inst.* 80:1553-1559, 1988
Shinkai et al. *Cell* 68:855-868 1992
Spanopoulou *Genes & Development* 8:1030-1042, 1994
Sui et al., *Proc. Natl. Acad. Sci. USA* 99(6):5515-5520 (2002)
Sun et al. *PNAS* 84:214-218, 1987
Tuaillon et al. *PNAS* 90:3720-3724, 1993
Tuschl, T., *Nature Biotechnol.* 20:440-448 (2002)
Verhoeyan et al., *Science* 239:1534, 1988
Vukanovic, J.; Passaniti, A.; Hirata, T.; Traystman, R. J.; Hartley-Asp, B.; Isaacs, J. T. Antiangiogenic effects of the quinoline-3-carboxamidc linomide. Cancer Res 1993, 53, (8), 1833-7
Ward et al., *Nature* 341:544-546, 1989
Wood et al., *Nature* 314:446-449, 1985
Yang N—C, Ho W-M, Chen Y-H, Flu M-L. A convenient one step extraction of cellular ATP using boiling water for the luciferin-luciferase assay of ATP. Analytical Biochemistry 2002, 306, 323-327.
Younes M, Brown R W, Mody D R, Fernandez L, Laucirica R. GLUT1 expression in human breast carcinoma: correlation with known prognostic markers. Anticancer Res 1995; 15: 2895-8.
Younes M, Lechago L V, Lechago J. Overexpression of the human erythrocyte glucose transporter occurs as a late event in human colorectal carcinogenesis and is associated with an increased incidence of lymph node metastases. Clin Cancer Res 1996a; 2: 1151-4.
Youncs M, Lechago L V, Somoano J R, Mosharaf M, Lechago J. Wide expression of the human erythrocyte glucose transporter Glut 1 in human cancers. Cancer Res 1996b; 56: 1164-7.
Yu et al., *Proc. Natl. Acad. Set. USA* 99(9):6047-6052 (2002)
Zeng et al., *Mol. Cell.* 9:1327-1333 (2002)

I claim:

1. A method for treating a person or animal, said method comprising administering an antibody, or antigen binding fragment thereof, that binds to glucose transporter-1 (Glut-1) protein, wherein the person or animal has breast or lung cancer.

2. The method according to claim 1, wherein said antibody or antigen binding fragment is administered prior to, subsequent to, or in combination with an anticancer agent, and/or with radiation therapy, and/or with surgical treatment.

3. The method according to claim 2, wherein said anti-cancer agent is administered, and wherein said anti-cancer agent is altretamine, bleomycin, bortezomib, busulfan, calcium folinate, capecitabine, carboplatin, carmustine, chlorambucil, cisplatin, cladribine, crisantaspase, cyclophosphamide, cytarabine, dacarbazine, dactinomycin, daunorubicin, docetaxel, doxorubicin, epirubicin, etoposide, fludarabine, fluorouracil, gefitinib, gemcitabine, hydroxyurea, idarubicin, ifosfamide, imatinib, irinotecan, liposomal doxorubicin, lomustine, melphalan, mercaptopurine, methotrexate, mitomycin, mitoxantrone, oxaliplatin, paclitaxel, pentostatin, procarbazine, raltitrexed, streptozocin, tegafururacil, temozolomide, thiotepa, tioguanine/thioguanine, topotecan, treosulfan, vinblastine, vincristine, vindesine, vinorelbine, melphalan, alemtuzumab, cetuximab, gemtuzumab, iodine 131 tositumomab, rituximab, or trastuzumab.

4. The method according to claim 2, wherein said anticancer agent is administered and wherein said anti-cancer agent is a mitotic inhibitor, an alkylating agent, an antimetabolite, a DNA intercalator, a topoisomerase inhibitor, an antiangiogenic agent, or an antiestrogen.

5. The method according to claim 1, wherein the route of administration of said, antibody or antigen binding fragment is parenteral.

6. The method of claim 1, wherein said antibody or antigen binding fragment is administered prior to, subsequent to, or in combination with a chemotherapeutic agent.

7. The method of claim 6, wherein said chemotherapeutic agent comprises at least one agent from among: 2-Amino-6-Mercaptopurine; 13-cis-Retinoic Acid; 2-Chlorodeoxyadenosine (2-CdA); 5-fluorouracil (5-FU); 6-Thioguanine (6-TG); 6-Mercaptopurine (6-MP); Actinomycin-D; Aldesleukin; Alemtuzumab; Alitretinoin; All-transretinoic acid; Alpha interferon; Altretamine; Amethopterin; Amifostine; Aminoglutethimide; Anagrelide; Anastrozole; Arabinosylcytosine (Ara-C); Arabinosylcytosine liposomal; Arsenic trioxide; Asparaginase; All Trans-Retinoic Acid (ATRA); Bacillus Calmette-Guérin (BCG); Bis-chloroethylnitrosourea (BCNU); Bevacizumab; Bexarotene; Bicalutamide; Bleomycin; Bortezomib; Busulfan; C225; Calcium Leucovorin; Camptothecin-11 (CPT-11); Capecitabine: Carboplatin; Carmustine; Carmustine wafer; CCNU; Cetuximab; Chlorambucil; Cisplatin (CDDP); Citrovorum Factor; Cladribine; Cortisone; Cyclophosphamide; Cytarabine; Cytarabine liposomal; Dacarbazine; Dactinomycin; Darbepoetin alfa; Daunomycin; Daunorubicin; Daunorubicin hydrochloride; Daunorubicin liposomal; Denileukin diftitox; Dexamethasone; Dexamethasone acetate; Dexamethasone sodium phosphate; Dexrazoxane; DHAD; DIC; Docetaxel; Doxorubicin; Doxorubicin liposomal; DTIC; Epirubicin; Epoetin alfa; Erwinia L-asparaginase; Estramustine; Etoposide; Etoposide phosphate; Exemestane; Filgrastim; Floxuridine; Fludarabine; Fluorouracil; Fluoxymesterone; Flutamide; Folinic Acid; Fulvestrant; Gefitinib; Gemcitabine; Gemtuzumab ozogamicin; Imatinib; Goserelin; Granulocyte colony stimulating factor (G-CSF); Granulocyte macrophage colony stimulating factor (GM-CSF); Hexamethylmelamine (HMM); Hydrocortisone; Hydrocortisone sodium phosphate; Hydrocortisone sodium succinate; Hydroxyurea; Ibritumomab; Ibritumomab tiuxetan; Idarubicin; Ifosfamide; Imatinib mesylate; Imidazole Carboxamide; Interferon alpha (IFN-alpha); Interferon alfa-2a; Interferon alfa-2b; Interferon alfa-2b polyethylene glycol (PEG) conjugate; Interleukin-2 (IL-2); Interleukin-11 (IL-11); Irinotecan; Isotretinoin; L-asparaginase; Letrozole; Leucovorin; Leuprolide; Leurocristine (LCR); Lomustine; L-PAM; L-Sarcolysin; Mechlorethamine; Mechlorethamine hydrochloride: Megestrol; Megestrol Acetate; Melphalan; Mercaptopurine; Mesna; Methotrexate (MTX); Methotrexate Sodium; Methylprednisolone; Mitomycin; Mitomycin C (MTC); Mitoxantrone; Mustine; Nilutamide; Nitrogen Mustard; Octreotide; Octreotide acetate; Oprelvekin; Oxaliplatin; Paclitaxel; Pamidronate; PEGylated interferon; Pegaspargase; Pegfilgrastim; PEG-L-asparaginase; Phenylalanine Mustard; Prednisolone; Prednisone; Procarbazine; Prolifeprospan 20 with carmustine implant; Raloxifene; Rituximab; Rubidomycin hydrochloride; Sargramostim; STI-571; Streptozotocin; Tamoxifen; Temozolomide; Teniposide; TESPA; Thalidomide; Thioguanine; Thiophosphoamide; Thiotepa; Topotecan; Toremifene; Trastuzumab; Tretinoin; TSPA; Vinblastine (VLB); Vinblastine Sulfate; Vincristine (VCR); Vinorelbine; Vinorelbine tartrate; VP-16; and Zoledronic acid.

8. The method of claim 6, wherein said chemotherapeutic agent comprises at least one agent from among cisplatin, paclitaxel, and gefitinib.

9. The method of claim 1, wherein said antibody or antigen binding fragment is administered to the person.

10. The method of claim 1, wherein the person or animal has breast cancer.

11. The method of claim 1, wherein the person or animal has lung cancer.

12. The method of claim 1, wherein the person or animal has non-small cell lung cancer (NSCLC).

13. The method of claim 9, wherein the person has breast cancer.

14. The method of claim 9, wherein the person has lung cancer.

15. The method of claim 9, wherein the person has non-small cell lung cancer (NSCLC).

16. The method of claim 5, wherein the route of administration of said antibody or antigen-binding fragment is intravenous.

17. A method for inhibiting the survival or proliferation of a breast cancer cell or lung cancer cell, said method comprising contacting said breast cancer cell or lung cancer cell with an effective amount of an antibody, or antigen binding fragment thereof, that binds to glucose transporter-1 (Glut-1) protein.

18. The method according to claim 17, wherein the breast cancer cell or lung cancer cell is a human cell.

19. The method of claim 17, wherein the cell is a breast cancer cell.

20. The method of claim 17, wherein the cell is a lung cancer cell.

21. The method of claim 17, wherein the cell is a non-small cell lung cancer (NSCLC) cell.

22. A method for treating breast cancer in a person or animal having the breast cancer, said method comprising parenterally administering a therapeutically effective amount of an antibody, or antigen binding fragment thereof, that binds to glucose transporter-1 (Glut-1) protein.

23. The method of claim 22, wherein said antibody or antigen binding fragment is administered intravenously.

24. The method of claim 22, wherein said antibody or antigen binding fragment is administered to a person.

25. The method of claim 22, wherein said antibody or antigen binding fragment is administered prior to, subsequent to, or in combination with an anticancer agent.

26. The method of claim 22, wherein said antibody is a monoclonal antibody.

\* \* \* \* \*

UNITED STATES PATENT AND TRADEMARK OFFICE
CERTIFICATE OF CORRECTION

PATENT NO. : 8,999,326 B2
APPLICATION NO. : 12/673677
DATED : April 7, 2015
INVENTOR(S) : George R. Simon It is certified that error appears in the above-identified patent and that said Letters Patent is hereby corrected as shown below:

In The Specification

Column 3,
Line 67, "ontological" should read --oncological--.

Column 6,
Lines 29-30, "ontological" should read --oncological--.

Column 10,
Line 60, "VII," should read --VH,--.
Line 64, "VII" should read --VH--.

Column 11,
Line 4, "VII" should read --VH--.

Column 12,
Line 9, "say" should read --scFv--.

Column 13,
Line 39, "earlier" should read --carrier--.
Line 56, "such as) sucrose," should read --such as sucrose,--.

Column 15,
Line 28, "earner." should read --carrier.--.

Column 17,
Line 66, "Epoctin alfa" should read --Epoetin alfa--.

Signed and Sealed this
Fifteenth Day of March, 2016

Michelle K. Lee
*Director of the United States Patent and Trademark Office*

Column 18,
Line 64, "composition or the" should read --composition of the--.

Column 20,
Line 21, "2×SDS" should read --2X SDS--.
Line 45, "(40×/0.75" should read --(40X/0.75--.
Lines 51-52, "climethylthiazol" should read --dimethylthiazol--.

Column 22,
Line 10, "F11650" should read --H1650--.

Column 23,
Line 55, "(MIT)" should read --(MTT)--.
Line 58, "MIT" should read --MTT--.

Column 24,
Line 21, "20/20°" should read --$20/20^n$--.
Line 59, "MDA-Mb-231" should read --MDA-MB-231--.

Column 25,
Line 19, "Aid" should read --Akt--.

Column 27,
Line 39, "*Mot Cell.*," should read --*Mol. Cell.*,--.
Line 45, "Cheliappan," should read --Chellappan,--.
Line 57, "Zaxnore," should read --Zamore,--.

Column 28,
Line 21, "quinoline-3-carboxamidc" should read --quinoline-3-carboxamide--.
Line 21, "Cancer Res" should read --*Cancer Res*--.
Line 25, "Yang N—C," should read --Yang N-C,--.
Line 25, "Flu M-L." should read --Hu M-L.--.
Line 38, "Youncs" should read --Younes--.

In The Claims

Column 29,
Line 9, "said, antibody" should read --said antibody--.